(12) United States Patent
Holmes et al.

(10) Patent No.: US 8,467,897 B2
(45) Date of Patent: Jun. 18, 2013

(54) PHARMACEUTICAL STORAGE AND RETRIEVAL SYSTEM AND METHODS OF STORING AND RETRIEVING PHARMACEUTICALS

(75) Inventors: William K. Holmes, San Diego, CA (US); Michael James, Vista, CA (US); Thomas F. Gaasch, Encinitas, CA (US)

(73) Assignee: RXSAFE LLC, San Diego, CA (US)

( * ) Notice: Subject to any disclaimer, the term of this patent is extended or adjusted under 35 U.S.C. 154(b) by 364 days.

(21) Appl. No.: 12/870,045

(22) Filed: Aug. 27, 2010

(65) Prior Publication Data

US 2011/0054668 A1 Mar. 3, 2011

Related U.S. Application Data

(63) Continuation-in-part of application No. 12/808,748, filed as application No. PCT/US2008/087858 on Dec. 19, 2008.

(60) Provisional application No. 61/091,261, filed on Aug. 22, 2008, provisional application No. 61/015,119, filed on Dec. 19, 2007.

(51) Int. Cl.
G06F 7/00 (2006.01)
G06F 17/00 (2006.01)

(52) U.S. Cl.
USPC .......... 700/216; 700/237; 700/236; 700/231; 700/240; 700/244

(58) Field of Classification Search
None
See application file for complete search history.

(56) References Cited

U.S. PATENT DOCUMENTS

| | | | |
|---|---|---|---|
| 4,019,793 A | 4/1977 | Gerding | |
| 4,267,942 A | 5/1981 | Wick, Jr. et al. | |
| 4,546,901 A | 10/1985 | Buttarazzi | |
| 4,635,053 A | 1/1987 | Banks et al. | |
| 4,695,954 A | 9/1987 | Rose et al. | |
| 5,047,948 A | 9/1991 | Turner | |
| 5,208,762 A | 5/1993 | Charhut et al. | |
| 5,337,919 A | 8/1994 | Spaulding et al. | |
| 5,593,267 A | 1/1997 | McDonald et al. | |
| 5,671,592 A | 9/1997 | Yuyama et al. | |
| 5,797,515 A | 8/1998 | Liff et al. | |
| 5,883,806 A | 3/1999 | Meador et al. | |
| 5,893,697 A | 4/1999 | Zini et al. | |
| 5,905,653 A | 5/1999 | Higham et al. | |

(Continued)

FOREIGN PATENT DOCUMENTS

WO 2009086217 7/2009

OTHER PUBLICATIONS

PCT/US2011/049543 International Search Report and Written Opinion dated Apr. 9, 2012 (14 pages).

*Primary Examiner* — Gene Crawford
*Assistant Examiner* — Yolanda Jones
(74) *Attorney, Agent, or Firm* — Michael Best & Friedrich LLP

(57) ABSTRACT

A pharmaceutical storage and retrieval system and a method of storing and retrieving pharmaceutical containers from the system. The system includes a pharmaceutical storage and retrieval and a controller operatively coupled to the device to control storage and retrieval functions of the device. The device includes a gantry assembly, a shelving assembly, a user access assembly, and a user authorization system that function in a coordinated manner to carry out the storage and retrieval functions of the device.

14 Claims, 31 Drawing Sheets

U.S. PATENT DOCUMENTS

| | | | |
|---|---|---|---|
| 5,907,493 | A | 5/1999 | Boyer et al. |
| 6,036,812 | A | 3/2000 | Williams et al. |
| 6,175,779 | B1 | 1/2001 | Barrett |
| 6,364,517 | B1 | 4/2002 | Yuyama et al. |
| 6,449,927 | B2 | 9/2002 | Hebron et al. |
| 6,604,019 | B2 | 8/2003 | Ahlin et al. |
| 6,609,047 | B1 | 8/2003 | Lipps |
| 6,650,964 | B2 | 11/2003 | Spano, Jr. et al. |
| 6,883,681 | B1 | 4/2005 | Coughlin et al. |
| 6,963,791 | B1 | 11/2005 | Frederick et al. |
| 7,006,893 | B2 | 2/2006 | Hart et al. |
| 7,151,982 | B2 | 12/2006 | Liff et al. |
| 7,182,105 | B1 | 2/2007 | Feehan et al. |
| 7,210,598 | B2 | 5/2007 | Gerold et |
| 7,228,198 | B2 | 6/2007 | Vollm et al. |
| 7,263,410 | B1 | 8/2007 | Frederick et al. |
| 7,263,411 | B2 | 8/2007 | Shows et al. |
| 7,289,879 | B2 | 10/2007 | William et al. |
| 7,316,536 | B2 | 1/2008 | Evans et al. |
| 7,630,788 | B1 | 12/2009 | Reese |
| 8,121,725 | B2 * | 2/2012 | Baker et al. ............... 700/236 |
| 8,342,400 | B1 | 1/2013 | Reese |
| 2004/0176873 | A1 | 9/2004 | Kim |
| 2005/0113968 | A1 | 5/2005 | Williams et al. |
| 2005/0234591 | A1 | 10/2005 | Kim |
| 2005/0263537 | A1 | 12/2005 | Gerold et al. |
| 2006/0041330 | A1 * | 2/2006 | Ansari et al. ............... 700/240 |
| 2006/0058918 | A1 | 3/2006 | Handfield et al. |
| 2007/0043469 | A1 * | 2/2007 | Draper ............... 700/231 |
| 2010/0030667 | A1 | 2/2010 | Chudy et al. |

\* cited by examiner

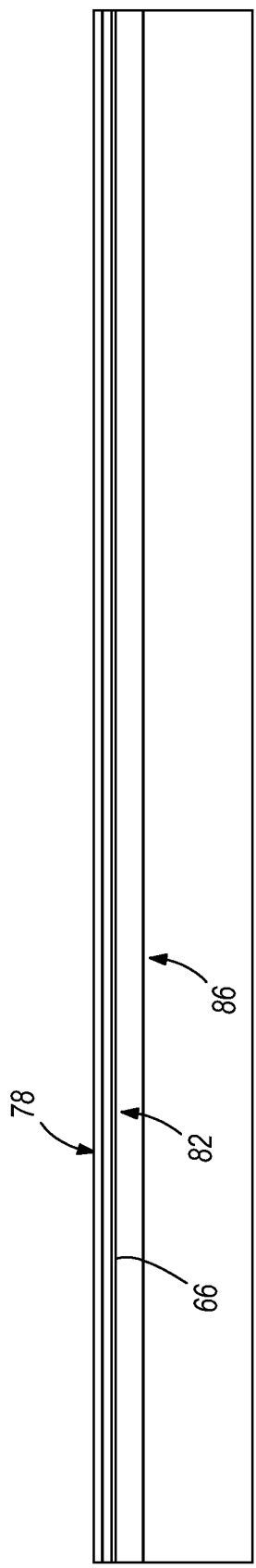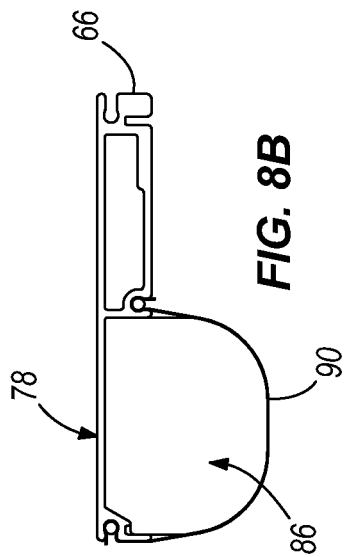
FIG. 8A
FIG. 8B

PHARMACEUTICAL STORAGE AND RETRIEVAL SYSTEM AND METHODS OF STORING AND RETRIEVING PHARMACEUTICALS

RELATED APPLICATIONS

This application is a continuation-in-part application of U.S. patent application Ser. No. 12/808,748, filed on Jun. 17, 2010, which is a 35 U.S.C. §371 application of international application number PCT/US2008/087858, filed on Dec. 19, 2008, which claims priority to U.S. Provisional Patent Application Ser. No. 61/091,261, filed on Aug. 22, 2008, and U.S. Provisional Patent Application Ser. No. 61/015,119, filed on Dec. 19, 2007. The contents of the above-listed applications are incorporated herein by reference.

BACKGROUND OF THE INVENTION

Many modern pharmacies continue to store their bulk pharmaceutical inventory on open shelves. These shelves are usually stocked and accessible by multiple technicians, clerks, and pharmacists. Such shelving arrangements are an inefficient use of space and make accurate monitoring of inventory challenging. Additionally, tracking the usage of particular prescription medication and determining when that medication needs restocking takes deliberate attention despite the use of currently available automated inventory monitoring systems. Currently available inventory monitoring systems are often inaccurate because such systems rely on assumptions. Further, even when such systems are used, unauthorized persons may have access to and misappropriate or mishandle the inventory.

As shown in FIG. 1, a typical pharmacy workflow generally includes three processes: (1) a front end process; (2) a filling process; and (3) a storage, selling, verification of prescription accuracy, and consulting with customer process. The front end process generally includes a clearinghouse aspect and drug utilization review where an intake worker receives insurance information, verifies that the prescription is valid, and inputs the necessary information into the pharmacy management system. The filling process includes filling a prescription by a pharmacy technician or pharmacist who obtains a bottle of medication from the shelf, pours the medication on a counting pad, counts the appropriate number of pills, pours the pills into a vial, labels the vial, prints the supporting consumer medication information, bags the vial and literature, and places the bag in a dispensing area. The third process includes a pharmacist verifying that the correct medication is in the customer vial when compared to the prescription, collecting money from the customer for the prescription, and consulting with the customer regarding usage and side effects of the medication. If a pharmacist has not already discussed the medication with the customer, a pharmacist must offer to do so during this third process in accordance with the State Board of Pharmacy regulations.

SUMMARY OF THE INVENTION

The present invention relates to a storage and retrieval system and method, and more particularly to a pharmaceutical storage and retrieval device and associated methods. The pharmaceutical storage and retrieval device includes a multi-operator, multi-mode interface that utilizes minimal input from operators, and functions in a secure multi-mode state. The pharmaceutical storage and retrieval device identifies authorized operators through RFID credentials and/or other assigned identification methods. The pharmaceutical storage and retrieval device controls the type and quantity of medication dispensed by identifying the medication dispensed, through, for example, bar code scanning, and determining the amount of medication dispensed by, for example, calculating the weight of a container from which medication has been dispensed. Accordingly, embodiments of the invention allow pharmacies to reduce transaction costs by improving inventory control, and by improving the speed and accuracy with which pharmacy technicians can fill prescriptions.

The features of the pharmaceutical storage and retrieval device include RFID operator identification, flexible multi-user operability, and a multi-mode state. These features are described below.

RFID Operator Identification: Each operator of the pharmaceutical storage and retrieval device is assigned a unique RFID credential (and/or other identification). Typically, each operator is assigned his or her unique RFID credential at the start of each shift. The RFID credential is activated and associated with a particular operator after the operator's identity is verified, by, for example, biometric authentication including: fingerprint verification, iris recognition, voice recognition, facial recognition, or a combination thereof. The RFID credential is scanned each time an operator interacts with the pharmaceutical storage and retrieval device to retrieve ("check-out") or return ("check-in") a container of medicine. The RFID credential is also scanned each time the operator interacts with the pharmaceutical storage and retrieval system to access or input data into the system. The RFID credential can be in the form of a bracelet (reusable or disposable) that is permanently or temporarily assigned to an operator. Alternatively, the RFID can be configured to expire after a certain period of time.

Flexible Multi-User Operability: Operators can be added or redeployed as needed to increase or reduce device capacity to about 100 filled prescriptions per operator per hour. There is no particular limit to the number of operators that can simultaneously use the pharmaceutical storage and retrieval device. Practically speaking, a pharmacy may not need more than three to five operators (e.g., 300-500 prescriptions/hour) to handle peak volumes.

Multi-Mode State: The pharmaceutical storage and retrieval device is configured to "check in" and "check out" prescription stock containers based on barcode scanning. When an operator scans a pre-printed prescription label and RFID credential at the device, either the container output port will open and the operator can retrieve the desired container, or the operator will be prompted to retrieve the prescription stock container from a remote stock location. While the prescription stock container is outside of the device, regardless of whether it came from inside the device or from remote stock, it is "checked out" or assigned to the operator who requested it based on the barcode scan and RFID scan.

Once an operator finishes with a container, it remains "checked out" until it is rescanned and put into the open container input port or remote stock location. The container is then reweighed, assigned a new pill/package count, and returned to stock. Remote stock containers can also be reweighed on an external scale before being manually returned to a remote stock location.

For some embodiments, rather than alter a retail pharmacy's existing workflow (which is generally illustrated in FIG. 1), the pharmaceutical storage and retrieval device is configured to integrate into an existing pharmacy's workflow with minimal disruption. FIG. 2 generally illustrates a retail pharmacy's workflow with the pharmaceutical storage and retrieval device according to one embodiment of the invention. The pharmaceutical storage and retrieval device facilitates the management of pharmaceutical inventories by automating the checking of prescription stock containers into and out of the system. The pharmaceutical storage and retrieval device further allows retail pharmacies to more effectively respond to fluctuations in prescription medication demand by easily allowing additional operators to be added to the pharmacy workflow at times of peak demand. Accordingly, retail pharmacies can reduce transaction costs by improving inventory control, and by improving the speed and accuracy with which pharmacy technicians can fill prescriptions. Furthermore, the pharmaceutical storage and retrieval device is designed to seamlessly integrate into existing pharmacies and is "drop-in" capable, such that costly workflow analyses and pharmacy redesigns are not necessary.

In one embodiment, the system can hold about 5,400 prescription containers that are quickly accessible to the user. The system 10, as shown in FIG. 3, maintains security of the containers while being flexible and customization to accommodate different pharmacies and their unique workflows. The system 10 is accessible through a user interface to adjust certain operational parameters of the system based on how each pharmacy wishes to use the system.

In one embodiment, the invention provides a pharmaceutical storage and retrieval system comprising: a housing including a gantry assembly, a user access assembly, and a user authorization system; and a controller operatively connected to the gantry assembly, the user access assembly, and the user authorization system, the controller including a computer having a computer readable medium configured to store instructions that when executed cause the controller to, read a user credential via the user authorization system, read a unique identifier on a prescription order to determine a container needed to fill a prescription on the prescription order, associate the user credential with the unique identifier, and transmit an instruction to the gantry assembly to retrieve the container and position the container in the user access assembly.

In another embodiment, the invention provides a pharmaceutical storage and retrieval system comprising: a housing including a gantry assembly, a user access assembly, and a user authorization system; and a controller operatively connected to the gantry assembly, the user access assembly, and the user authorization system, the controller including a computer having a computer operable medium configured to store instructions that when executed cause the controller to, read a user credential at the user authorization system, read a unique identifier on a container, associate the user credential with the unique identifier, and transmit an instruction to the gantry assembly to retrieve the container from the user access assembly and position the container in the housing.

In another embodiment, the invention provides a pharmaceutical storage and retrieval system comprising: a housing including a shelving assembly supported by the housing, the shelving assembly including a plurality of shelves, each shelf extending along a length of the housing, the plurality of shelves positioned from a bottom wall of the housing to a top wall of the housing with a predetermined space between adjacent shelves, each shelf having a top surface and a bottom surface, and wherein one of the top surface and the bottom surface of a shelf is partially covered with a foam, the foam configured to conform to a container as the container is inserted between two adjacent shelves to hold the container in its position.

Other aspects of the invention will become apparent by consideration of the detailed description and accompanying drawings.

BRIEF DESCRIPTION OF THE DRAWINGS

FIG. 8A is a front cross-sectional view of a shelf in the shelving assembly illustrated in FIG. 7.

FIG. 8B is a side cross-sectional view of a shelf in the shelving assembly illustrated in FIG. 7.

DETAILED DESCRIPTION

Figure 1:
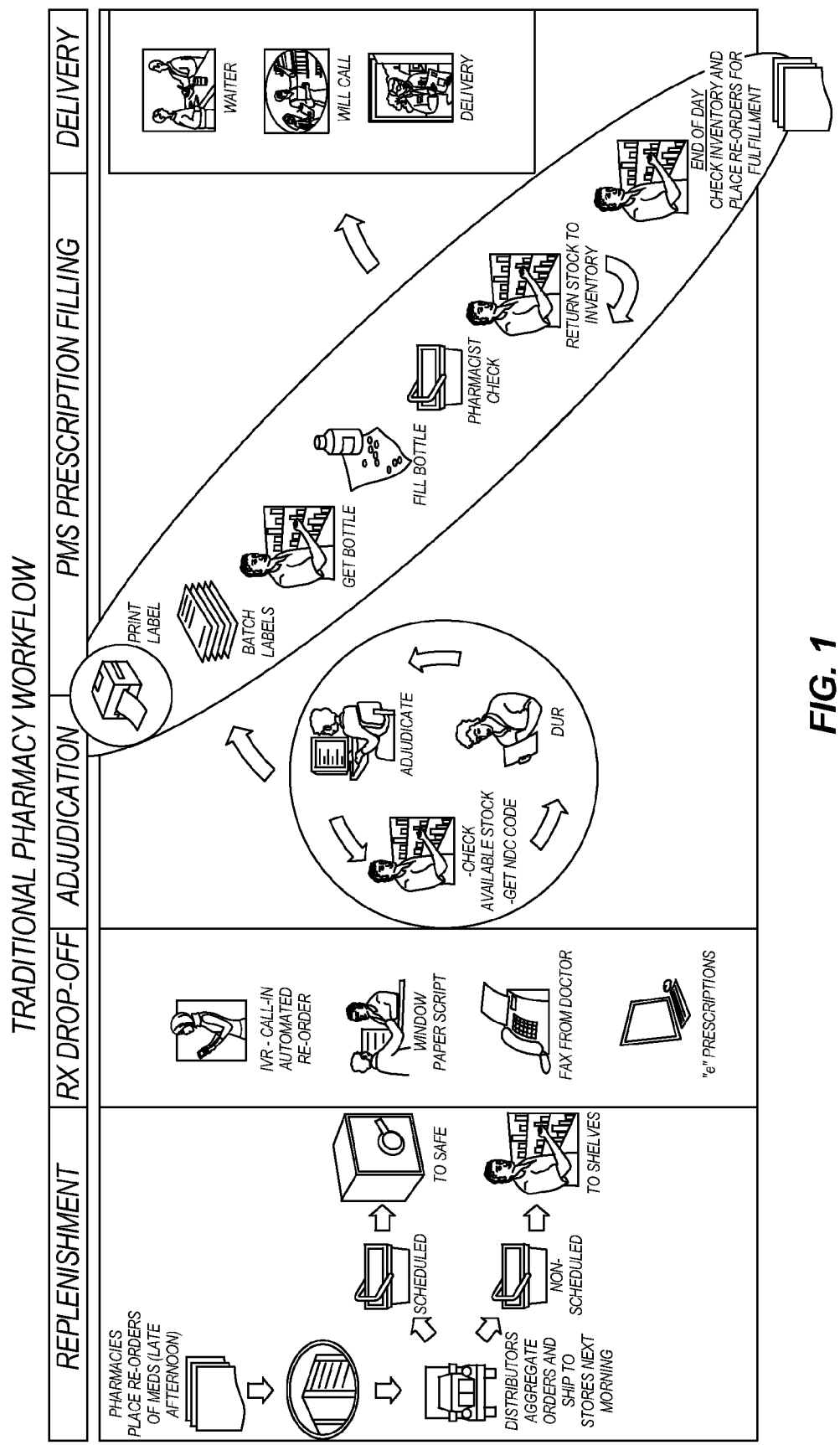
FIG. 1 is a chart illustrating a traditional pharmacy workflow.
Figure 2:
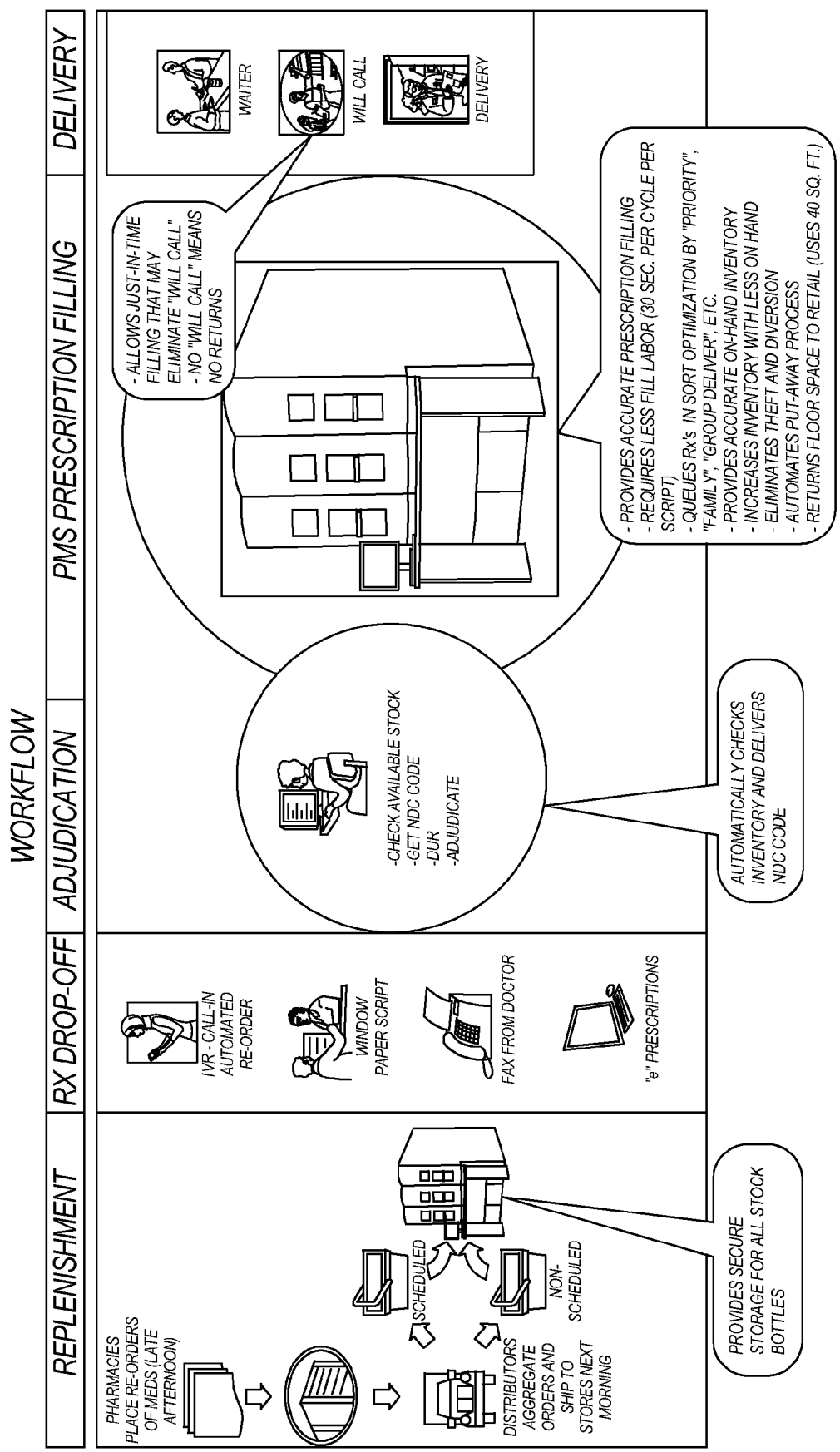
FIG. 2 is a chart illustrating a modified pharmacy workflow implementing a pharmaceutical storage and retrieval system according to one embodiment of the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components, may be utilized to implement the invention. Furthermore, and as described in subsequent paragraphs, the specific mechanical configurations illustrated in the drawings are intended to exemplify embodiments of the invention; other alternative mechanical configurations are possible.

Figure 3:
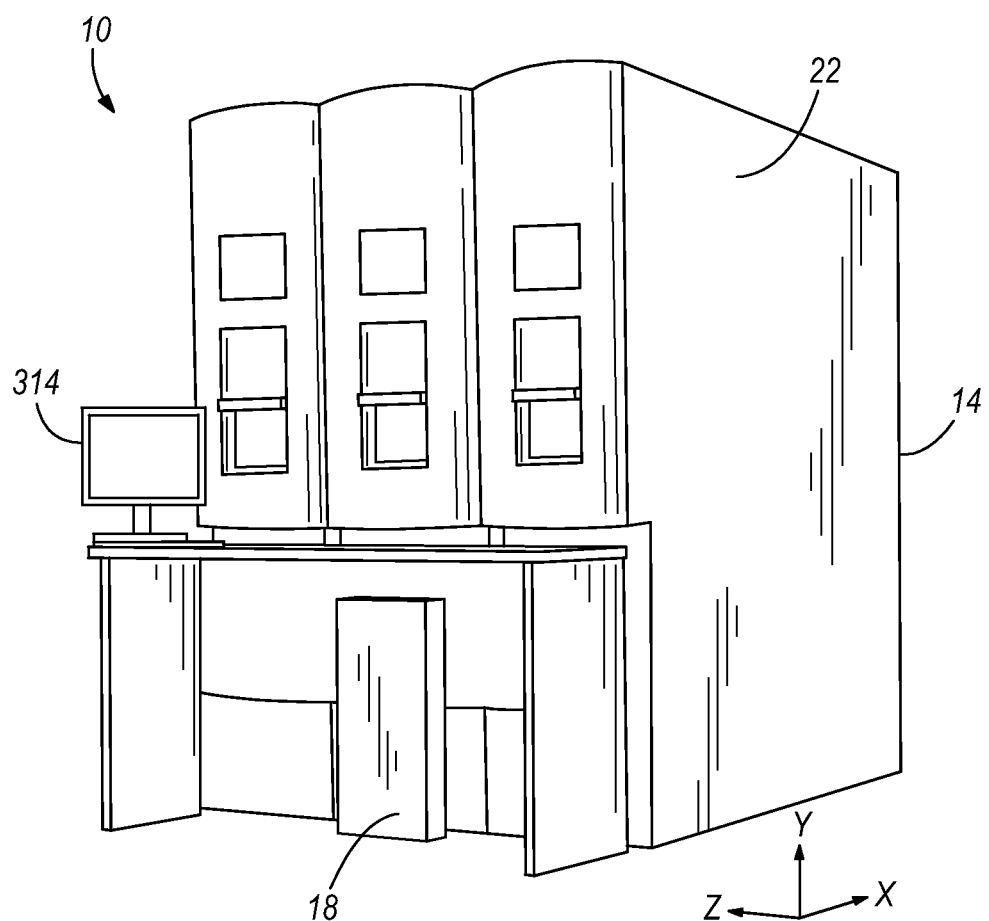
FIG. 3 is a perspective view of a pharmaceutical storage and retrieval system having three storage and retrieval devices according to one embodiment of the present invention.

FIG. 3 illustrates a pharmaceutical storage and retrieval system 10 according to one embodiment of the present invention. The pharmaceutical storage and retrieval system 10 is a comprehensive workflow automation and high density robotic storage system for use in retail pharmacies. The system 10 seamlessly dispenses prescription containers and returns them to inventory without requiring operators to use a complicated software interface.

As shown in FIG. 3, the pharmaceutical storage and retrieval system 10 includes one or more pharmaceutical storage and retrieval devices 14 and a computer or controller 18 configured to control the operations and functionality of the pharmaceutical storage and retrieval device 14. Although the system 10 shown in FIG. 3 includes three pharmaceutical storage and retrieval devices 14, more or fewer devices 14 can be utilized in a particular pharmaceutical storage and retrieval system 10.

Figure 4:
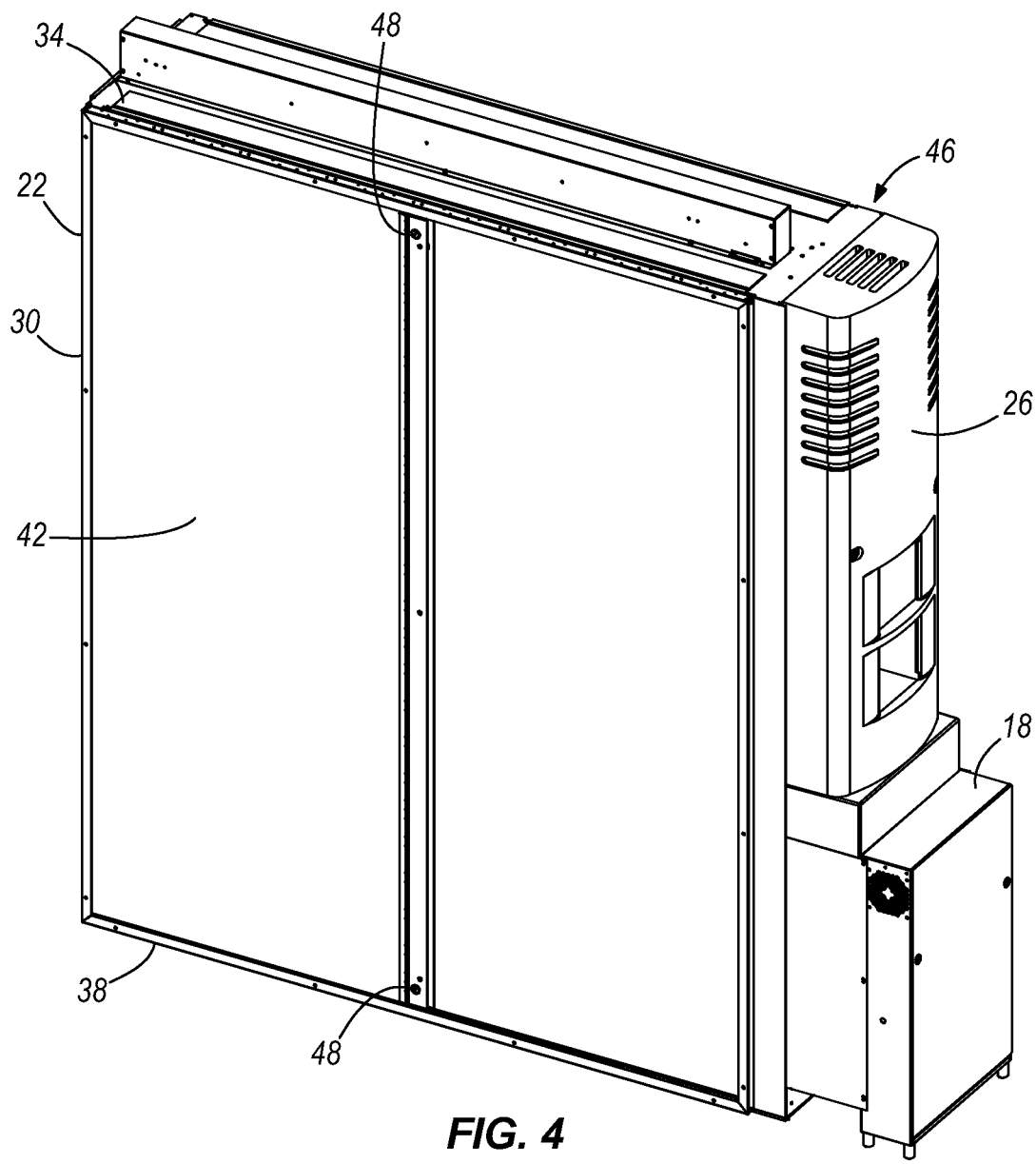
FIG. 4 is a left side perspective view of the middle storage and retrieval device of the pharmaceutical storage and retrieval system illustrated in FIG. 3.
Figure 5:
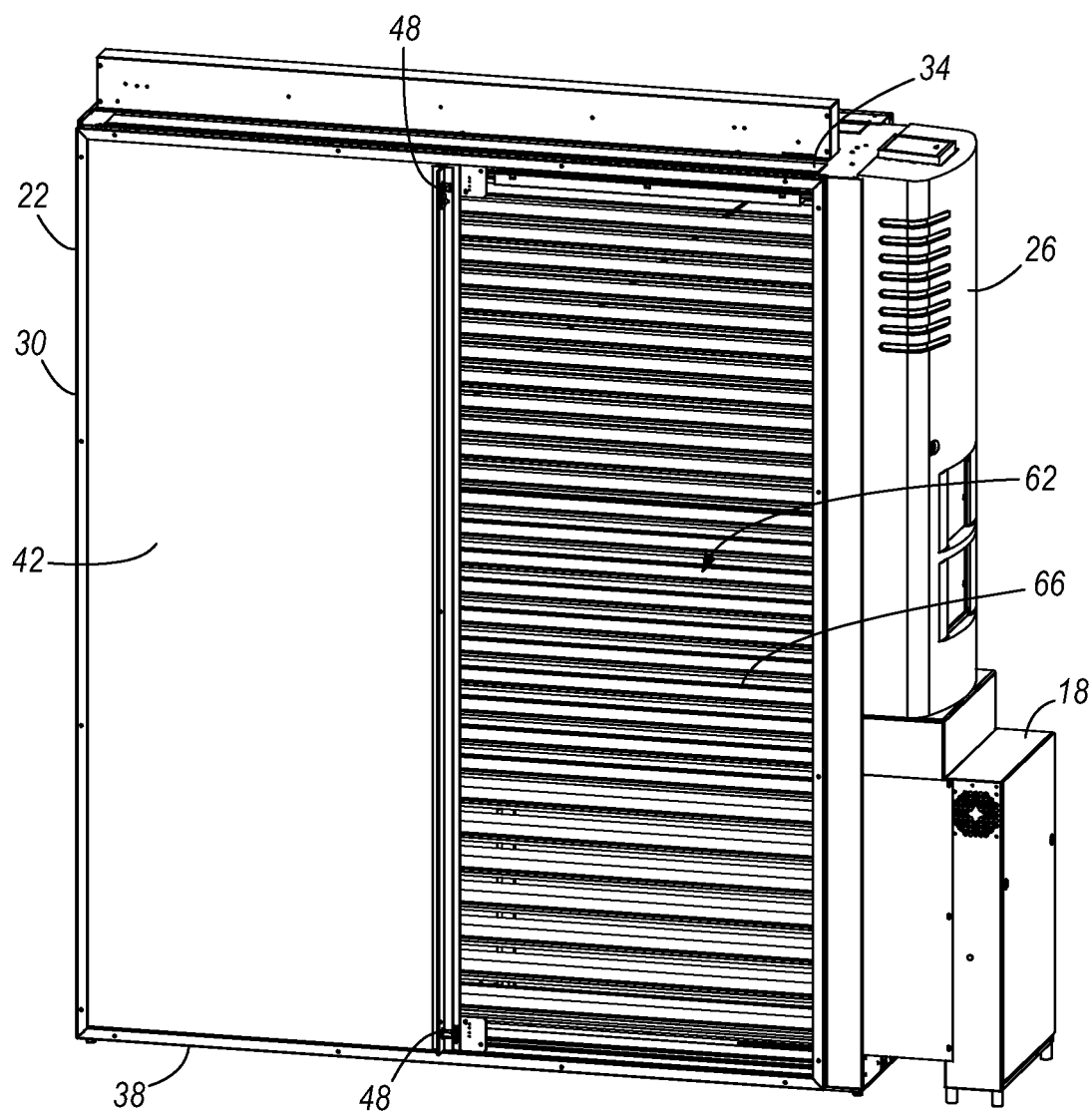
FIG. 5 is another left side perspective view of the middle storage and retrieval device of the pharmaceutical storage and retrieval system illustrated in FIG. 3.
Figure 6:
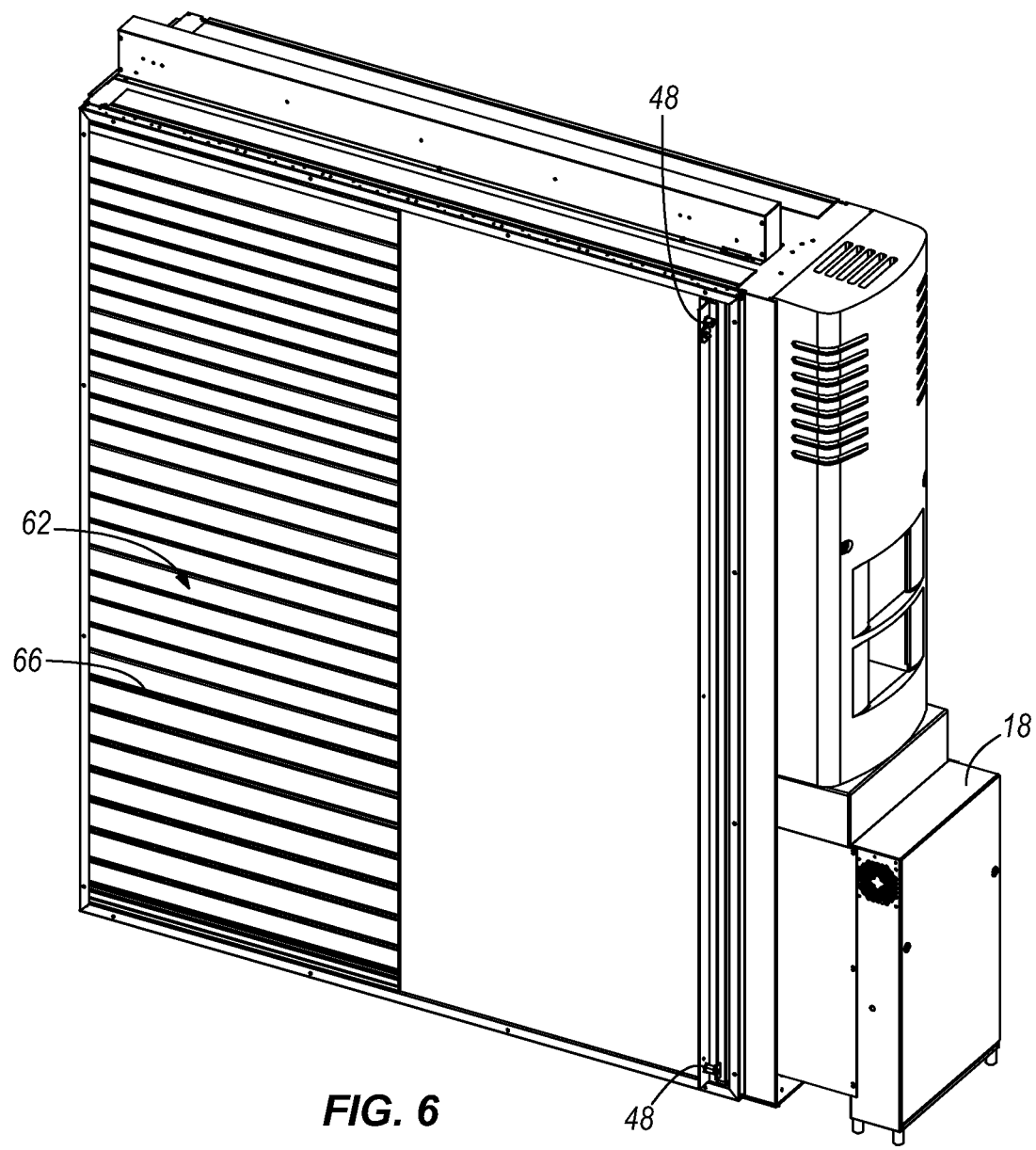
FIG. 6 is another left side perspective view of the middle storage and retrieval device of the pharmaceutical storage and retrieval system illustrated in FIG. 3.

With reference to FIGS. 3 and 4, the pharmaceutical storage and retrieval device 14 includes a housing 22 having a front wall 26, a rear wall 30, a top wall 34, a bottom wall 38, a first side wall 42, and a second side wall 46. As shown in FIGS. 4-6, the walls 26, 30, 34, 38, 42, 46 define a volume of space having a length along a first axis (x direction), a height along a second axis (y direction) substantially perpendicular to the first axis, and a width along a third axis (z direction) substantially perpendicular to both the first axis and the second axis. (See FIG. 3 for the coordinate system.)

As shown in FIGS. 4-6, the walls 42 and 46 are sliding access panels that allow operator access to the interior of the housing 22. In further embodiments, fewer or more walls 26, 30, 34, 38, 42, 46 of the housing may be moveable with respect to the remainder of the housing to allow access to the interior of the housing 22. In still further embodiments, the housing 22 may include other access panels or ports to allow controlled access to the interior of the housing 22. As further shown in FIGS. 4-6, the walls 42 and 46 include locks 48 to prevent movement of the walls relative to the remainder of housing 22, and unauthorized access to housing 22. In further embodiments each wall 26, 30, 34, 38, 42, 46 and any panel or port may include one or more locks 48, or other security device, to prevent unauthorized access to the interior of the housing. In still further embodiments, one or more of the locks 48 may be electronically controlled by the controller 18.

With reference to FIGS. 5-9, 17-28, and 32-33, the housing 22 is configured to support a shelving assembly 50, a gantry assembly 54, a user access assembly 58, and a user authorization system 362.

Shelving Assembly

Figure 7:
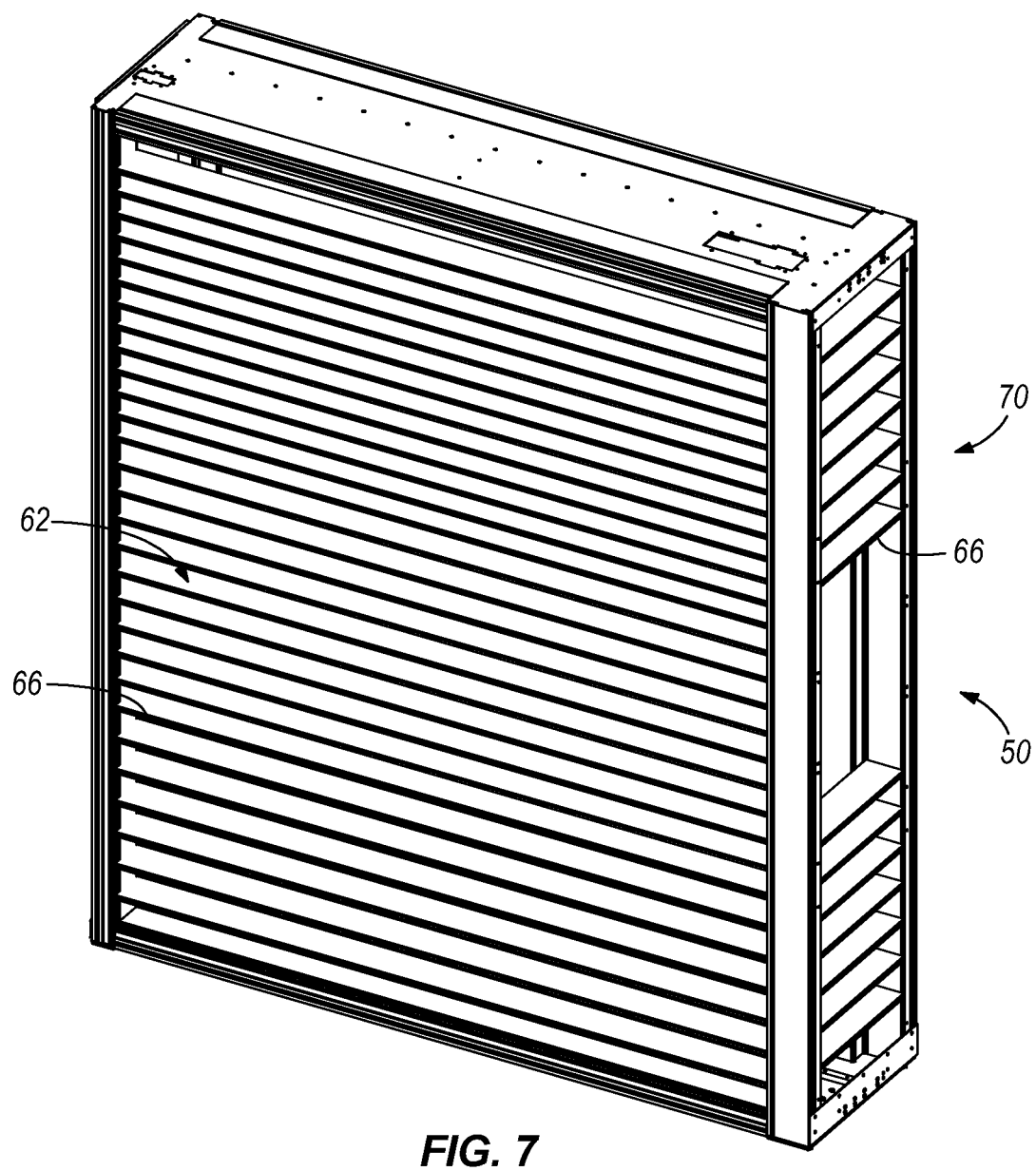
FIG. 7 is a side perspective view of a shelving assembly within the pharmaceutical storage and retrieval system illustrated in FIG. 3.

With reference to FIGS. 5-7, the shelving assembly 50 includes a first set 62 of shelves 66 positioned adjacent to the first side wall 42 and arranged along the height of the housing 22 from the top wall 34 to the bottom wall 38. The shelving assembly 50 also includes a second set 70 of shelves 66 positioned adjacent to the second side wall 46 and arranged along the height of the housing 22 from the top wall 34 to the bottom wall 38. The first set 62 of shelves 66 and the second set 70 of shelves 66 are separate and apart from each other, such that a gap exists between the first set 62 and the second set 70. This gap provides space for the gantry assembly 54 (shown in FIGS. 9 and 10) to operate.

With continued reference to FIGS. 5-7, each shelf 66 in the first set 62 and the second set 70 extends along the length of the housing 22, from the front wall 26 to the rear wall 30. Each shelf 66 in the first set 62 and the second set 70 also is positioned a predetermined distance along the second axis from an adjacent shelf 66. The shelves 66, in both the first set 62 and the second set 70, are adjustable to vary the distance between adjacent shelves 66 to accommodate differently-sized containers 94 (shown in FIG. 13). For example, the predetermined distance between the shelves 66 can vary from about three inches to about thirteen inches. Furthermore, the distances between shelves 66 in the first set 62 can be the same as or different than the distances between shelves 66 in the second set 70. Accordingly, the distances between the shelves 66 can be customized so that a wide variety of containers 94 including, for example, oversized containers and/or other unique packages, can be stored efficiently in the pharmaceutical storage and retrieval device 14.

The housing 22 further includes a third and fourth set of shelves 66 adjacent to the front wall 26. The third set of shelves 66 extend between the first side wall 42 and the second side wall 46 and are arranged along the height of the housing 22 between the bottom wall 38 and the user access ports on wall 26. The fourth set of shelves 66 extend between the first side wall 42 and the second side wall 46 and are arranged along the height of the housing 22 between the top wall 34 and the user access ports on wall 26. The third and fourth sets of shelves 66 allow for additional storage of pharmaceutical containers within the device 14 without restricting the movement of the gantry assembly 54. Further, the third and fourth sets of shelves 66 allow for the storage of relatively long containers that may not fit on the first set 62 and second set 70 of shelves 66, or that are longer than the gap between the first set 62 and second set 70 of shelves 66. The shelves 66, in both the third and fourth sets, are adjustable to vary the distance between adjacent shelves 66 to accommodate differently-sized containers 94. Furthermore, the distances between shelves 66 in the third set can be the same as or different than the distances between shelves 66 in the fourth set 70.

With reference to FIGS. 8A-8B, each shelf 66 of the shelving assembly 50 includes a top surface 78 and a bottom surface 82. The shelves 66 may further include a liner 86, made of foam, including, for example, commercially-available memory foam and covered with a fabric layer 90, attached to the bottom surface 82. In further embodiments, the foam liner 86 can be attached to the top surface 78 of a shelf 66. In still further embodiments, the foam liner 86 can be attached to both the top surface 78 and the bottom surface 82 of a shelf 66. The fabric layer 90 provides a smooth surface for the insertion and removal of a container on the shelf 66, and may be made of, for example, Lycra® or another suitable fabric in lieu of or in combination with Lycra®. When a container 94 is positioned on a shelf 66, the liner 86 conforms to the container 94 as it is inserted such that the container 94 remains in its position. As illustrated in FIGS. 8A-8B, the foam liner 86 is approximately two-inches thick and may be compressed more than two-thirds of its thickness to accommodate an inserted container 94. Accordingly, the liner 86 allows for a variety of container sizes to fit on a shelf 66 with a particular spacing. In further embodiments, the foam liner 86 can be thicker or thinner, and can be more or less compressible. As illustrated in FIG. 8B, the foam liner 86 covers approximately half of the width of a shelf 66. In further embodiments, the liner 86 can cover more or less of the width of the shelf 66. In addition, as each container 94 is positioned on a shelf 66, the system 10 maintains a gap between each container 94 such that the liner 86 remains undisturbed (or returns to its undisturbed state). After a container 94 is removed from a shelf 66, the liner 86 returns to its original position. Accordingly, the foam liners 86 allow the container 94 to be inserted into a specific position on a shelf 66 and removed from the shelf 66 without disturbing a neighboring container 94.

As discussed above, the shelving assembly 50 can accommodate a plurality of containers 94 regardless of size. In general, most containers 94 may have a body 98 with a circular or rectangular cross-section and a cap 102 with a circular cross-section that attaches to the body 98 to enclose pills, powder, and reconstituted and liquid forms of prescription medicines. (See FIGS. 13 and 14.) These containers 94 are inserted into position on the shelves 66 of the shelving system 50 on their sides. Other types of containers may have other shapes and include, for example, boxes, blister packs, syringes, bottles with dispensing cups or spoons, and vials that generally do not have a cap 102 with a circular cross-section (or no cap at all). Such irregularly shaped containers can be placed within a custom container (e.g., a metal or plastic box) having a cylindrical protrusion that resembles a circular cap 102 so that the pharmaceutical storage and retrieval device 14 can process the irregularly shaped container in a similar manner as it processes a container 94. Accordingly, discussion herein regarding the storage of containers 94 within the device 14 is equally applicable to the storage of pharmaceuticals that are placed in a custom container. The custom container can include one or more transparent or clear sides so the contents inside the custom container are visible. In other constructions, the custom container can include one or more opaque sides. By placing irregularly shaped containers (e.g., those without a circular cap 102) in a custom container having a cylindrical protrusion that resembles a circular cap 102 almost every type of pharmaceutical product can be stored in the pharmaceutical storage and retrieval device 14. With reference to particular types of pharmaceuticals, the security and access control features of pharmaceutical storage and retrieval device 14 allow for the safe storage of narcotics and other controlled pharmaceuticals within the device 14. In certain embodiments of the pharmaceutical storage and retrieval device 14, the device 14 further includes climate control mechanisms, including, for example, refrigeration to allow storage of temperature sensitive pharmaceuticals. Those pharmaceuticals or medical supplies that are excessively large (e.g., colonoscopy preparation jugs or boxes of sterile gloves) may be stored outside the pharmaceutical storage and retrieval device 14.

Generally, each pharmaceutical product delivered to a pharmacy includes a label 114 with a standardized bar code, which typically includes a National Drug Code number ("NDC"). The NDC is a unique 10 or 11-digit, 3-segment number that identifies the labeler, product, and trade package size of a drug product. The first segment, the labeler code, is assigned by the FDA. A labeler is any firm (including repackers or relabelers) that manufactures, or distributes (under its own name) the drug product. The second segment, the product code, identifies a specific strength, dosage form, and formulation for a particular firm. The third segment, the package code, identifies package sizes and types. Both the product and package codes are assigned by the firm. Typically, the pharmaceutical product can be identified by the NDC on the label 114. In instances where the pharmaceutical product does not include an NDC, the product may be identified by the standardized bar code. Accordingly, reference herein to the NDC and identification of a pharmaceutical product by its NDC applies to any standardized bar code that identifies the pharmaceutical product.

The pharmaceutical storage and retrieval device 14 is configured to accept pharmaceutical products that come in a standard container 94 (i.e., a container with a body 98 with a circular or rectangular cross-section and a cap 102 with a circular cross-section) and have a label 114 affixed to the body 98 of the container 94. As discussed above, pharmaceutical products that come in irregularly shaped containers may be placed within a custom container so that the pharmaceutical storage and retrieval device 14 can process the irregularly shaped container in the same way that it processes a container 94. In such circumstances, the irregularly shaped container having a label 114 may be placed within a custom container having at least one transparent side such that the label 114 can be read through the transparent side. Alternatively in some embodiments, a supplemental label with a unique identifier can be generated and attached to the custom container (with or without a transparent side) to identify and associate the irregularly shaped container(s), and the contents thereof, that are placed within the custom container. The supplemental label can be associated to the label 114 and stored in the system 10 so that when the custom container containing the irregularly shaped container is needed, the custom container can be located. In further embodiments, the custom container includes a permanent or semi-permanent unique identifier (e.g., barcode) that identifies characteristics of the custom container (e.g., dimension and weight of the custom container). In such embodiments, the permanent or semi-permanent unique identifier on the custom container can be associated with the label 114 of the pharmaceutical in the irregularly shaped container.

The pharmaceutical storage and retrieval device 14 is also configured to accept customer vials that are not picked up from the pharmacy. In many instances, pharmacies prepare and fill a prescription in anticipation of the customer arriving at the pharmacy to retrieve the customer's prepared vial of medication. In some instances, however, the customer is delayed or never comes to retrieve the prepared vial of medication. In such instances, the pharmacy must continue to store and track the customer's vial. If the customer does not retrieve the prepared vial, the pharmacy may use the prepared vial to fill a prescription for another customer. The pharmaceutical storage and retrieval device 14 can be used to manage customer vials that are not picked up from the pharmacy in a similar fashion to the way the device 14 manages other irregularly shaped containers. The customer vial can be placed in a custom container having a label or other unique identifier that identifies the custom container. The customer vial and the pharmaceutical contained therein can be associated with the label or unique identifier on the custom container. The label or other unique identifier on the custom container also can be associated with a lot number and an expiration date on the original pharmaceutical container from which the pharmaceutical was dispensed. Furthermore, the label or other unique identifier on the custom container can be associated with a specific transaction number that can identify the customer, the date the vial was filled, and other data related to the transaction. In certain instances, the customer vial can be of a size and construction such that a custom container is not required to hold the vial. In such instances, the customer vial can be handled by the system 10 as if it were a standard container 94.

A custom container can store different types of pharmaceuticals and previously-filled vials for different customers. Since each type of pharmaceutical and each customer vial can be linked to a label or other unique identifier associated with the custom container, the location of these particular pharmaceuticals and customer vials can always be located.

Gantry Assembly

Figure 9:
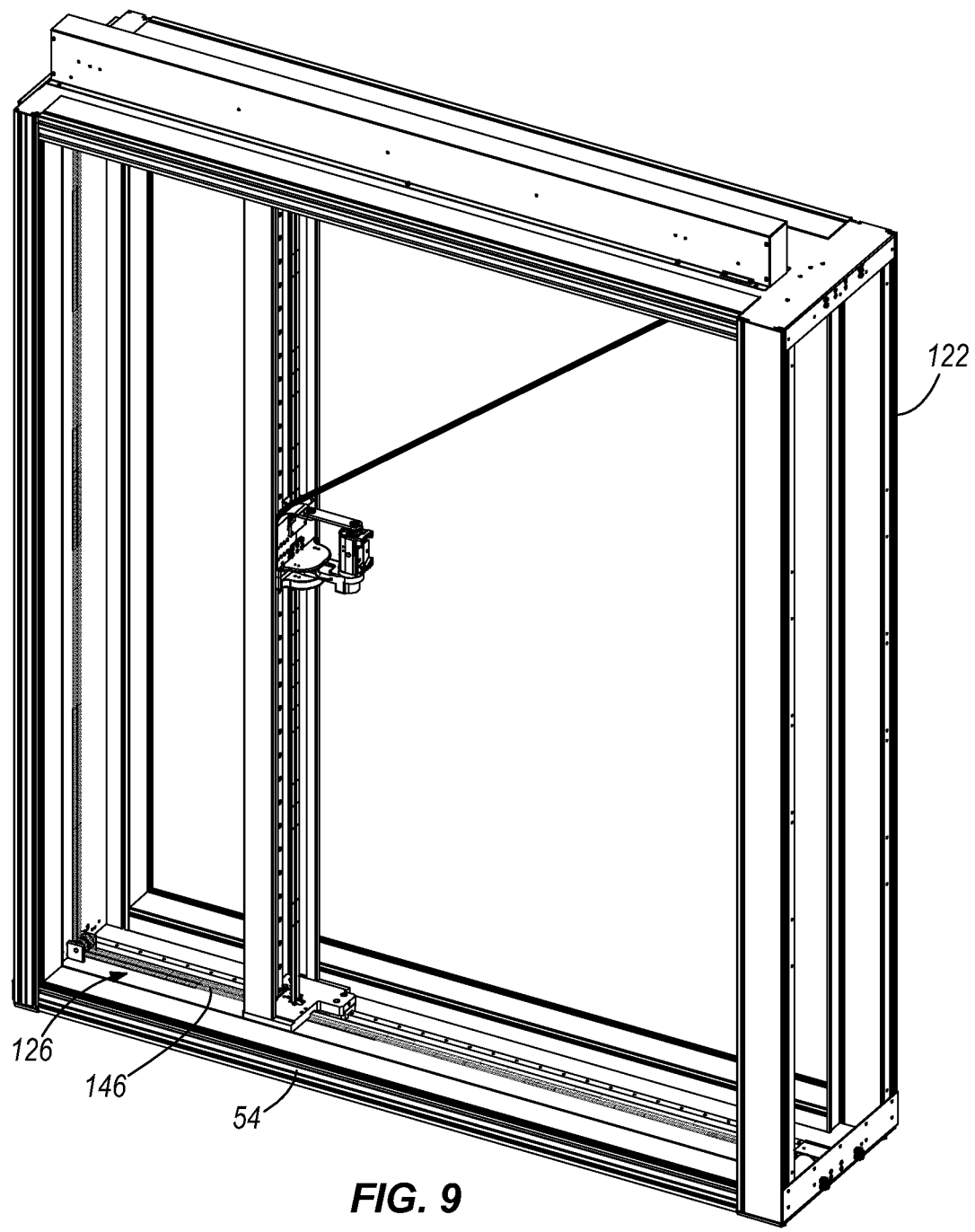
FIG. 9 is a perspective view of a gantry assembly of the pharmaceutical storage and retrieval system illustrated in FIG. 3.
Figure 10:
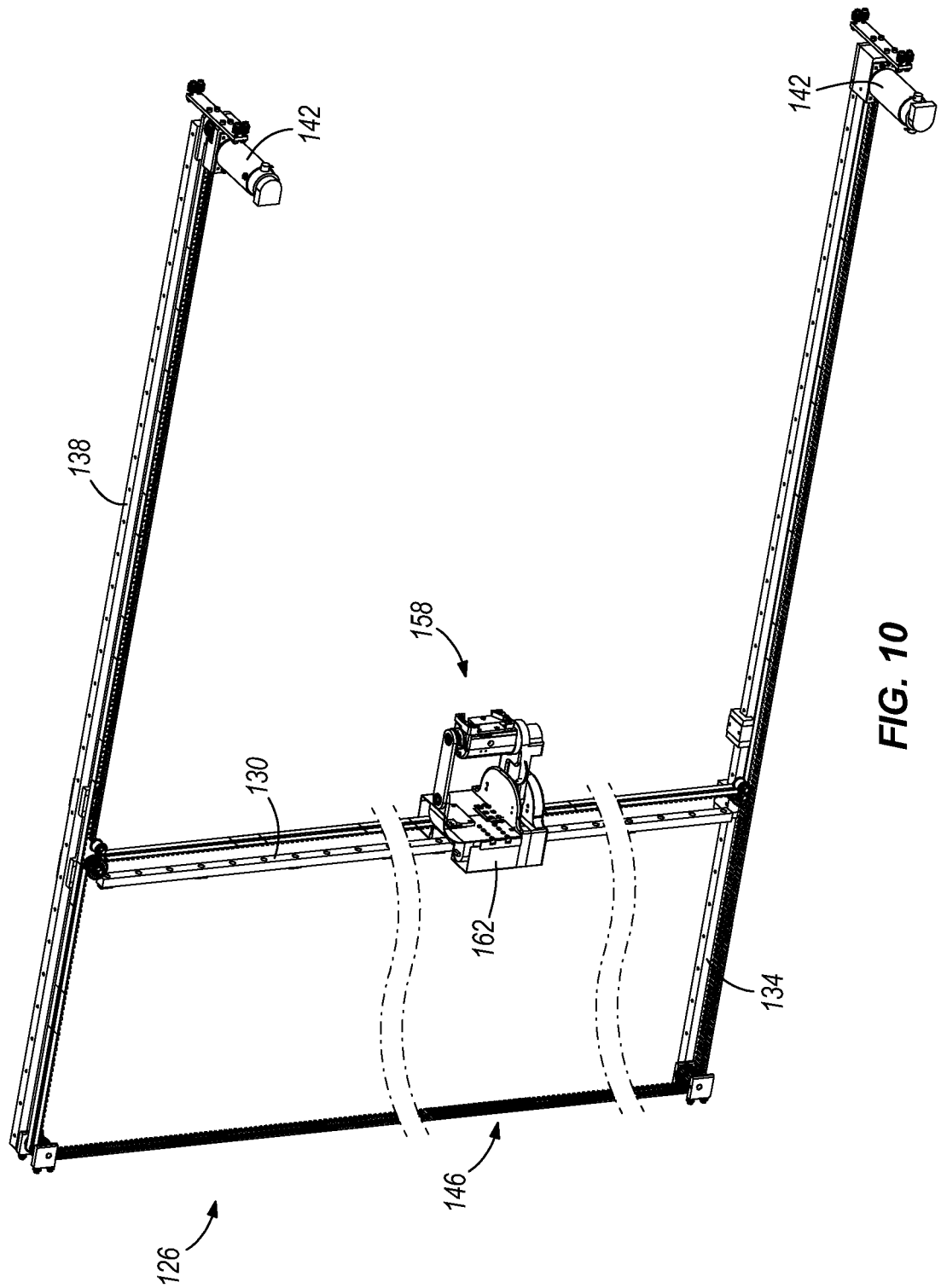
FIG. 10 is a perspective view of a track assembly of the pharmaceutical storage and retrieval device illustrated in FIG. 3.

The gantry assembly 54, illustrated in FIGS. 9-10, is supported by a frame 122 and includes a track assembly 126, a drive assembly 146, and a carriage assembly 158. As shown in FIG. 10, the track assembly 126 includes a generally vertical track 130 having a first end and a second end, a first generally horizontal track 134 adapted to support one of the first end and the second end of the track 130, and a second generally horizontal track 138 adapted to support one of the first end and the second end of the track 130. The track 130 is configured to travel along the first horizontal track 134 and the second horizontal track 138.

Figure 11:
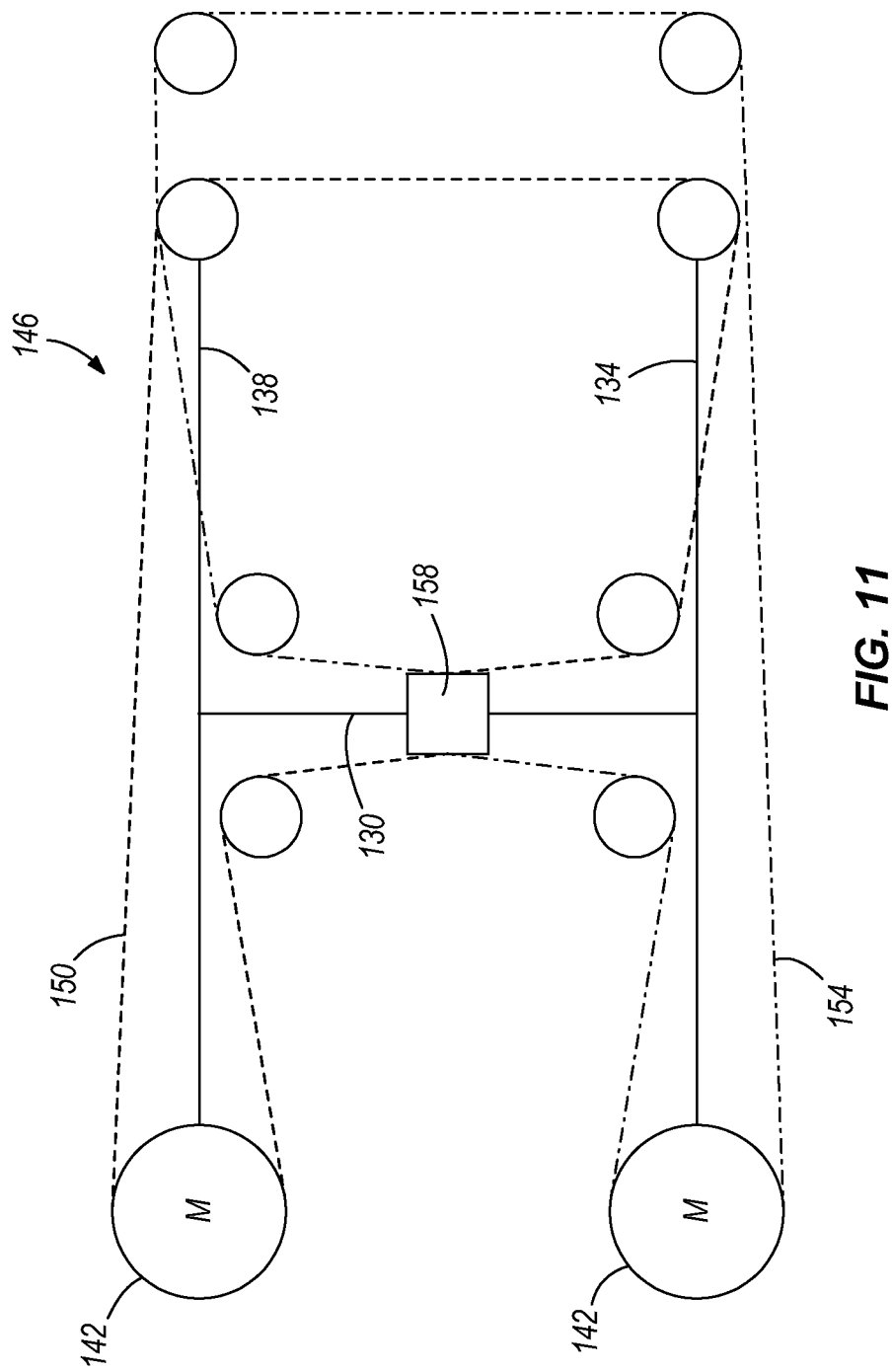
FIG. 11 is a schematic view of a belt assembly of the pharmaceutical storage and retrieval system illustrated in FIG. 3.

With reference to FIGS. 10 and 11, the drive assembly 146 includes a plurality of motors 142, a first belt circuit 150, a second belt circuit 154, and a plurality of pulleys. The motors 142 are connected to the first and second belt circuits 150, 154 to coordinate horizontal and vertical movement of the gantry assembly 54. Specifically, the coordinated operation of the motors 142 is used to move the vertical track 130 along the horizontal tracks 134, 138, and to move the carriage assembly 158 vertically along the vertical track 130. When both motors 142 rotate clockwise, the carriage assembly 158 moves in an upward direction along the vertical track 130. When both motors 142, shown in FIG. 11, rotate counter-clockwise, the carriage assembly 158 moves in a downward direction along the vertical track 130. When the motors 142 rotate in opposite directions, the vertical track 130 moves horizontally along the horizontal tracks 134, 138. The direction and speeds of the motors 142 can be controlled such that the vertical track 130 moves horizontally and the carriage assembly 158 moves vertically along the vertical track 130 resulting in a diagonal movement of the carriage assembly 158 within the device 14.

With reference to FIGS. 12-16, the carriage assembly 158 includes a first motor 162, a gripper assembly 166, and a second motor 174. The carriage assembly further includes a frame 182 that supports the gripper assembly 166 and gear assembly 186. The gear assembly 186 is coupled to the motors 162, 174 and includes a plurality of gears operable to rotate the gripper assembly 166 between a plurality of positions. The first motor 162 is operable to rotate the gripper assembly 166 through 180 degrees of rotation about a first axis 170. The second motor 174 is operable to rotate the gripper assembly 166 through 180 degrees of rotation about a second axis 178. Accordingly, the motors 162, 174 provide coordinated motion of the gripper assembly 166 to retrieve, position, and transport a container 94 between a shelf location and the user access assembly 58. The coordinated motion reduces the amount of space within the pharmaceutical storage and retrieval device 14 due to the reduced arc motion of the container 94 as the gripper assembly 166 retrieves and positions a container 94 from its shelf location. The coordinated motion of gripper assembly 166 can be further coordinated with the movement of the carriage assembly 158. In particular, the coordinated motion of the gripper assembly 166 can be coordinated with the horizontal movement of carriage assembly 158 as the vertical track 130 is moved horizontally by motors 142. The overall coordinated movement of the gripper assembly 166 and the carriage assembly 158 results in linear, or near linear movement of a container 94 held by the gripper assembly, such that a container may be inserted perpendicularly with respect to a shelf 66.

In further embodiments, the gripper assembly 166 may include linear actuators and linear drive mechanisms, instead of or in addition to the motors 162, 174 and the gear assembly 186 described above to move the gripper assembly. Such embodiments may include electrically and pneumatically driven motors and actuators.

Figure 12:
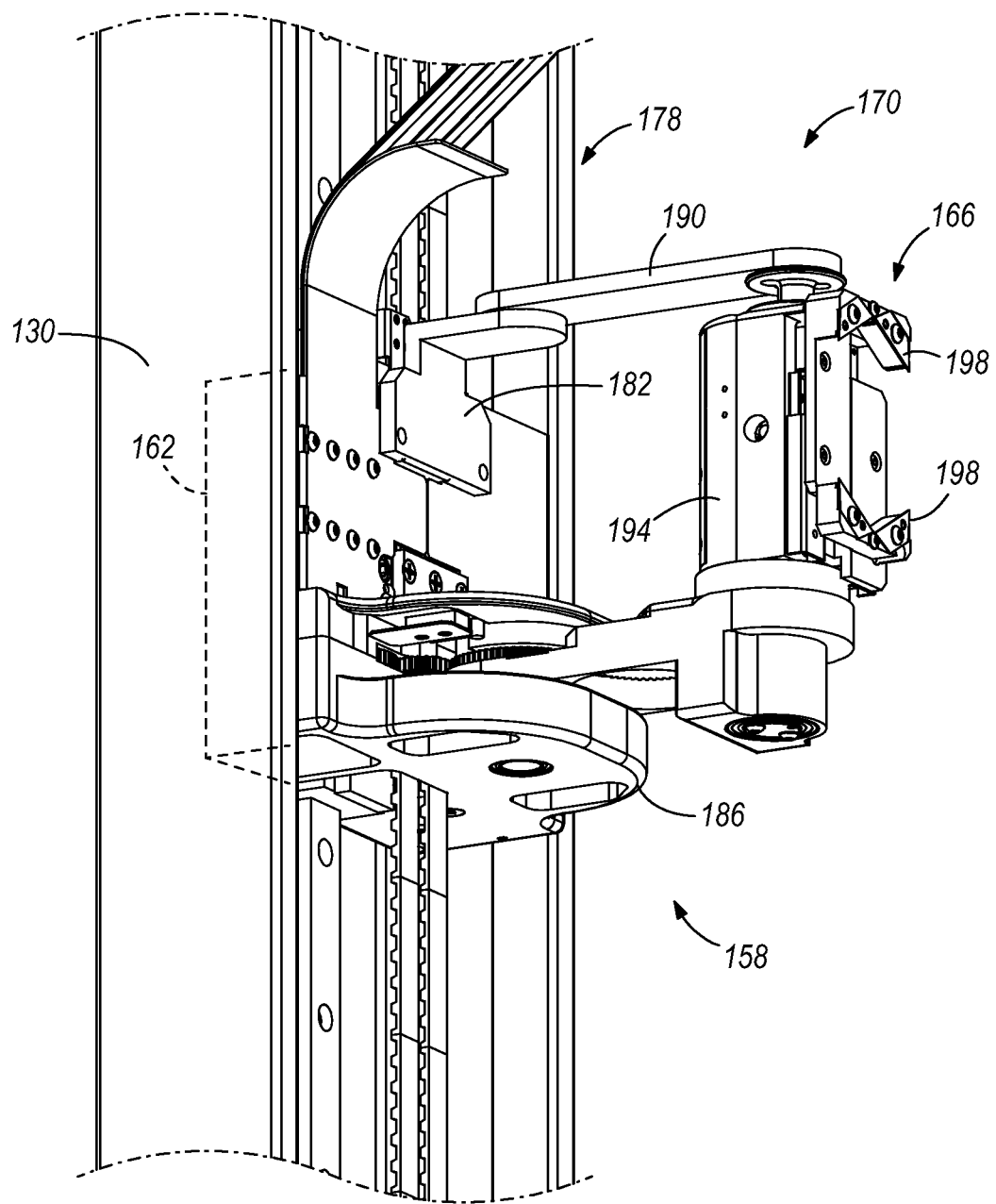
FIG. 12 is a perspective view of a carriage assembly of the pharmaceutical storage and retrieval system illustrated in FIG. 3.
Figure 13:
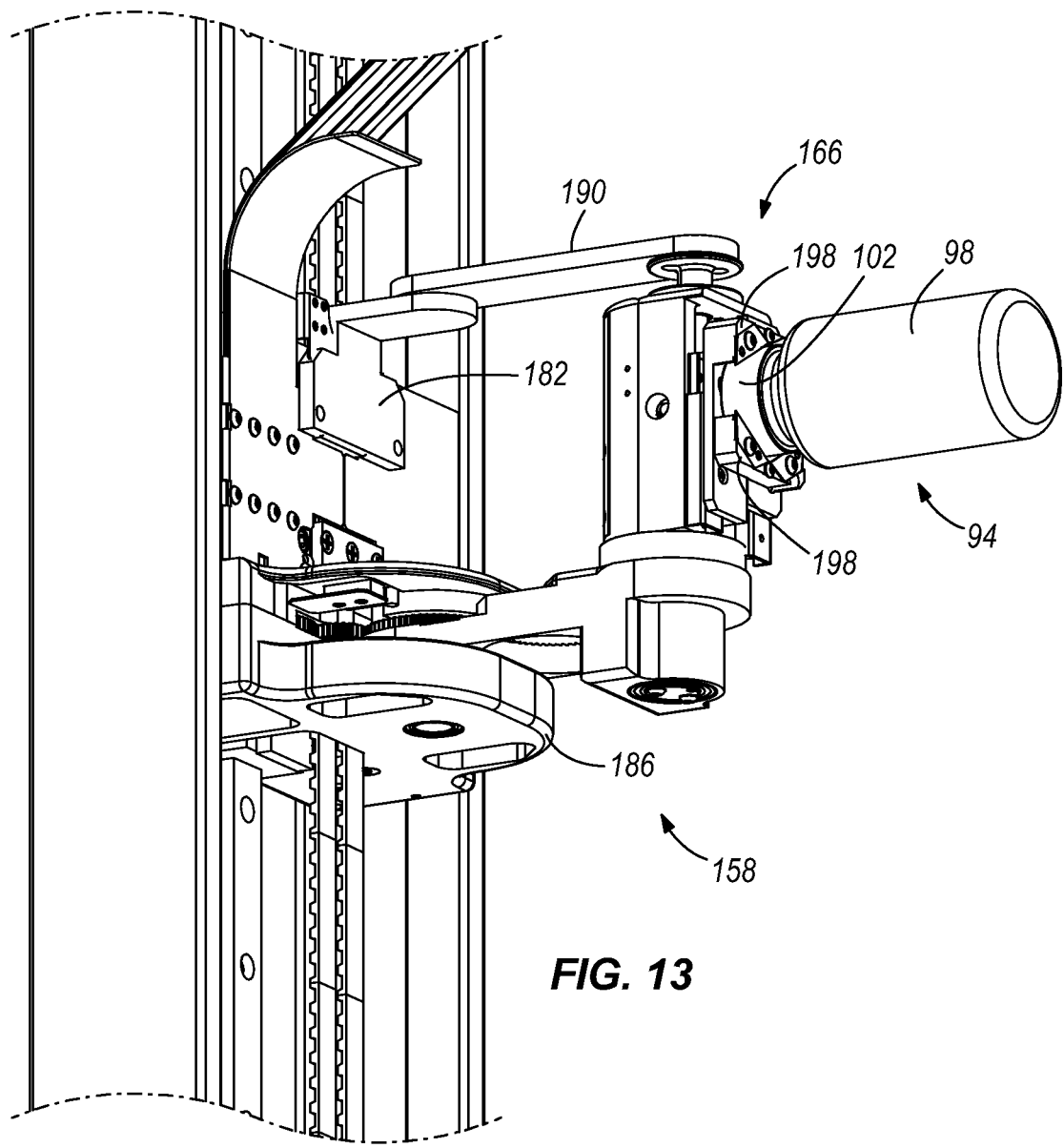
FIG. 13 is a perspective view of a carriage assembly of the pharmaceutical storage and retrieval system illustrated in FIG. 3 with a container.
Figure 14:
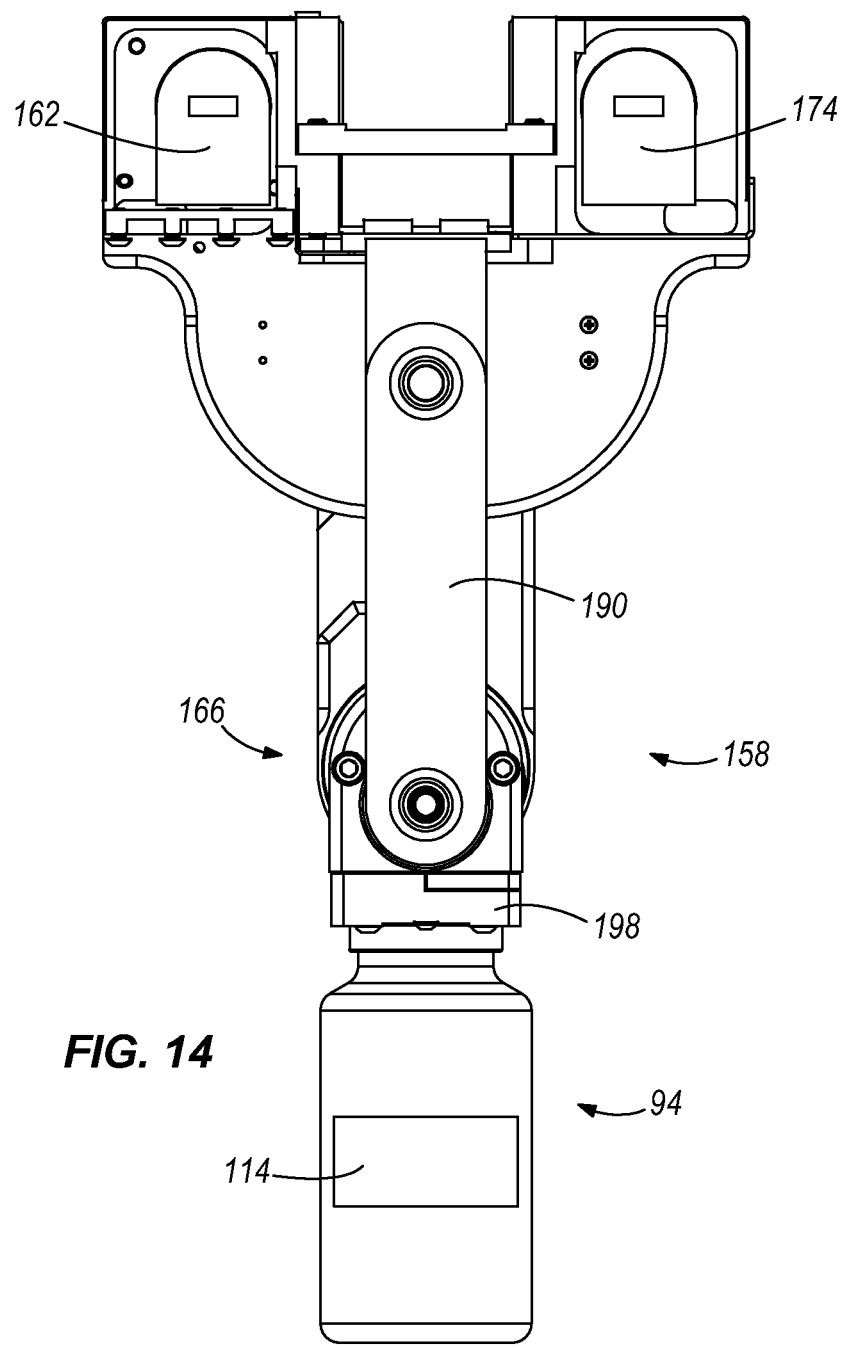
FIG. 14 is a top view of a carriage assembly of the pharmaceutical storage and retrieval device illustrated in FIG. 3 with a container.
Figure 15:
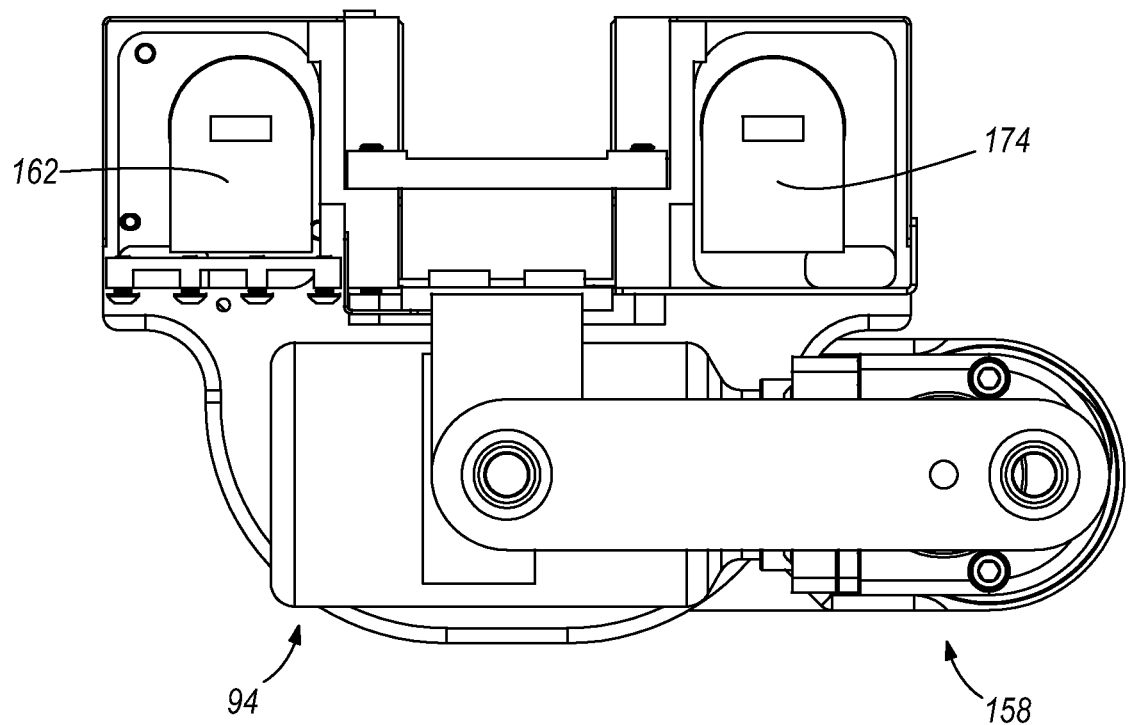
FIG. 15 is a top view of a carriage assembly of the pharmaceutical storage and retrieval system illustrated in FIG. 3 with a container.
Figure 16:
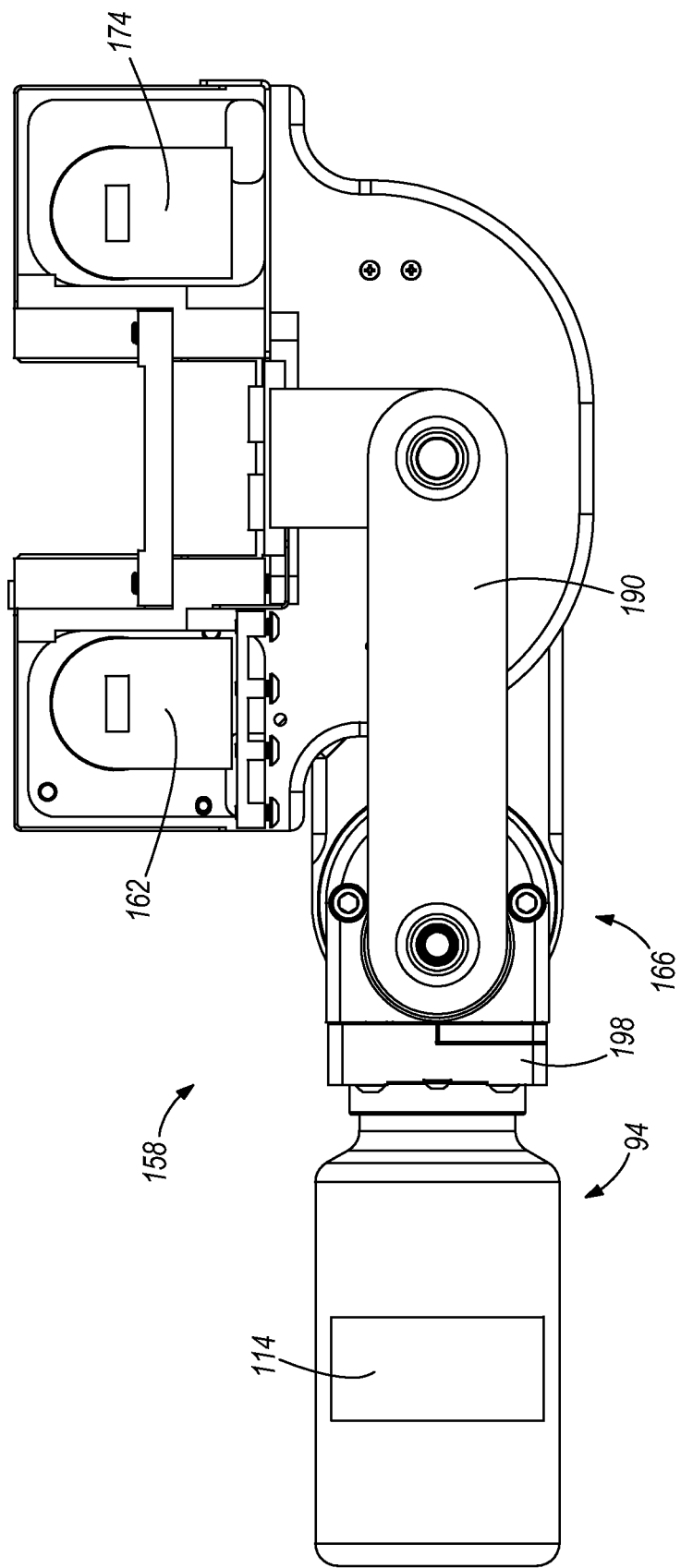
FIG. 16 is a top view of a carriage assembly of the pharmaceutical storage and retrieval system illustrated in FIG. 3.

With continued reference to FIGS. 12-16, the gripper assembly 166 includes a support member 190 pivotably coupled to the frame 182. The gripper assembly 166 also includes a motor 194 to move a plurality of fingers 198, which are operable to move between a first position and a second position to grip a container 94. The fingers 198 are configured to grasp caps 102 of different diameters, including, for example, caps 102 having diameters from 1-inch to 3-inches. In certain embodiments, the fingers 198 can include inserts, including for example, razor blades, blade edges, or spring steel strips. The inserts provide a sharp and hard surface so that the fingers 198 can engage a cap 102 (typically made of a hard plastic) and support the weight of a container 94 as the gantry assembly 54 retrieves a container. The inserts can be replaced as needed so that during service the fingers 198 maintain their grasping ability. FIG. 12 illustrates the carriage assembly 158 without the gripper assembly 166 holding a container. FIGS. 13-16 illustrate the carriage assembly 158 with the gripper assembly 166 holding a container 94. As illustrated in FIG. 13, the fingers 198 of the gripper assembly 166 grip the cap 102; however, it is noted that the fingers 198 can grip the container 94 at locations other than the cap 102. FIGS. 14-16 illustrate motion of the gripper assembly 166 through a series of steps in moving a container 94. FIG. 14 illustrates the gripper assembly 166 in a first position gripping a container 94 just retrieved from (or about to be positioned in) a particular location within the pharmaceutical storage and retrieval device 14. FIG. 15 illustrates the gripper assembly 166 in a second position (generally rotated about 90 degrees from the first position). While the gripper assembly 166 is in the second position, the carriage assembly 158 is operable to move along the vertical track 130, and the vertical track 130 is operable to move along the horizontal tracks 134, 138. The gripper assembly 166 may be in positions other than those illustrated in the figures when the carriage assembly 158 moves. FIG. 16 illustrates the gripper assembly 166 in a third position translated along a plane defined by the second position and a predetermined distance from the second position. In the third position, the gripper assembly 166 is positioned to insert a container 94 into or onto a shelf 66, or conversely to retrieve a container 94 from a shelf 66.

User Access Assembly

Figure 20:
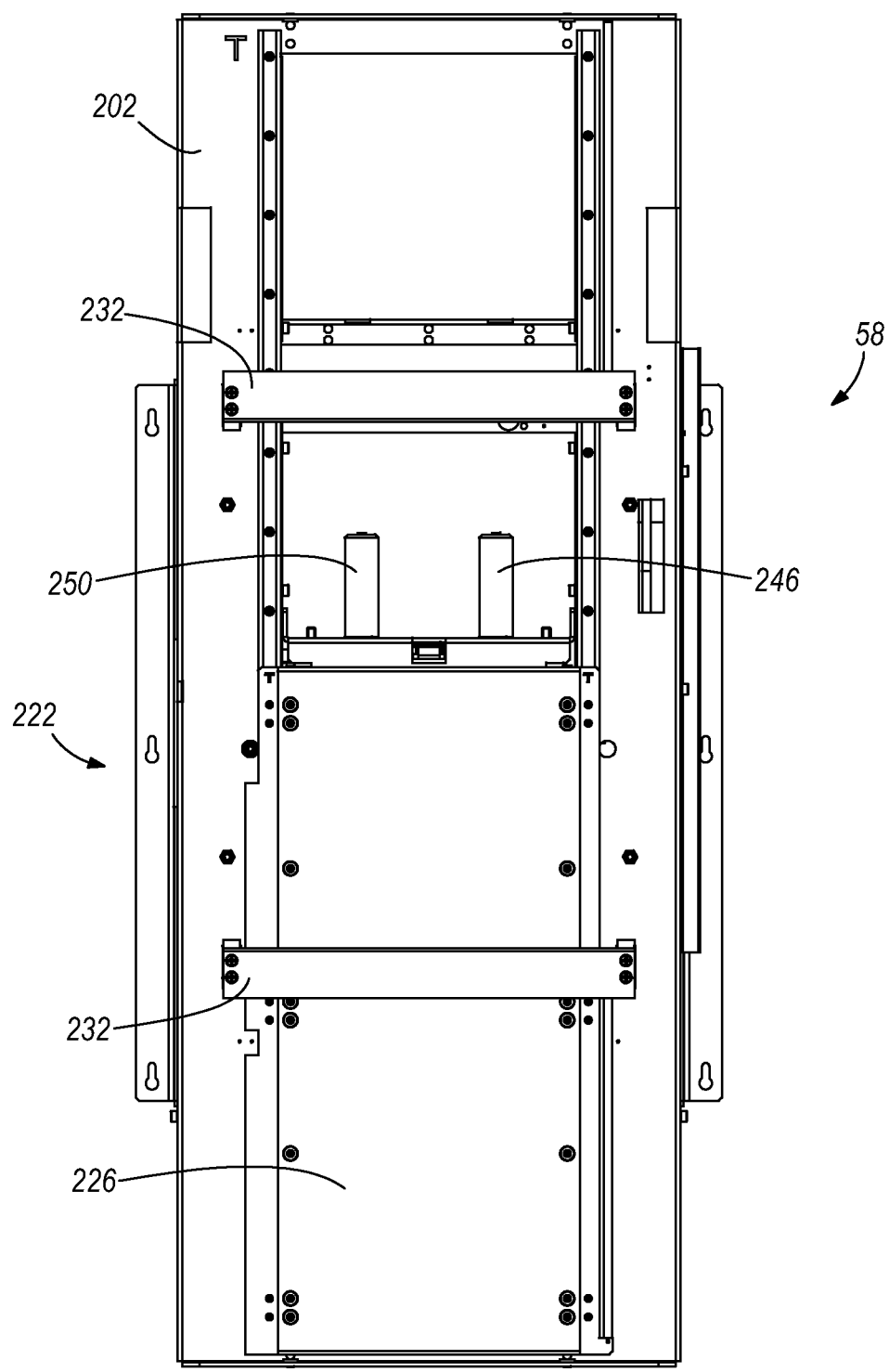
FIG. 20 is a front view of the user access assembly of the pharmaceutical storage and retrieval system illustrated in FIG. 3.
Figure 21:
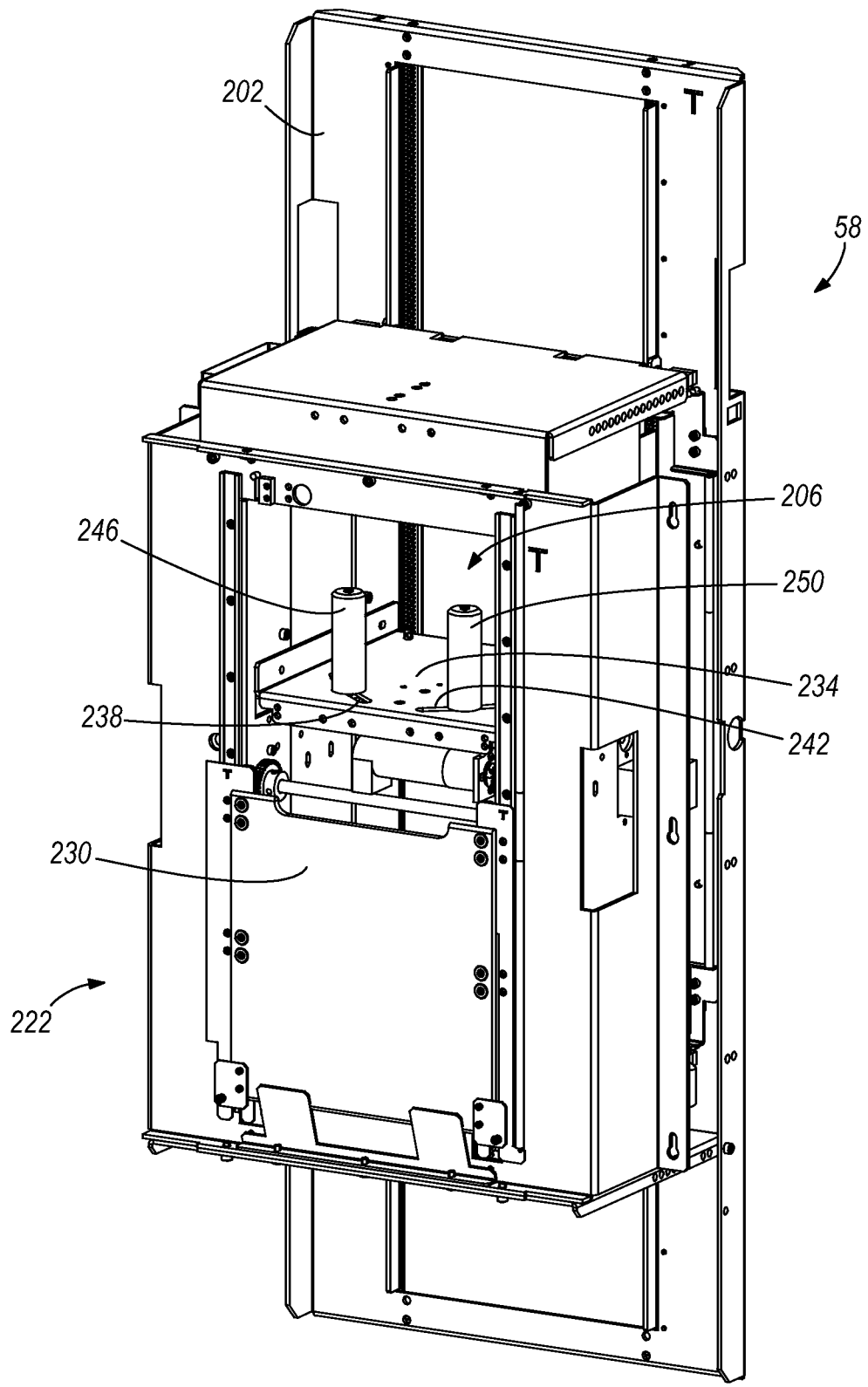
FIG. 21 is a rear perspective view of the user access assembly of the pharmaceutical storage and retrieval system illustrated in FIG. 3.
Figure 22:
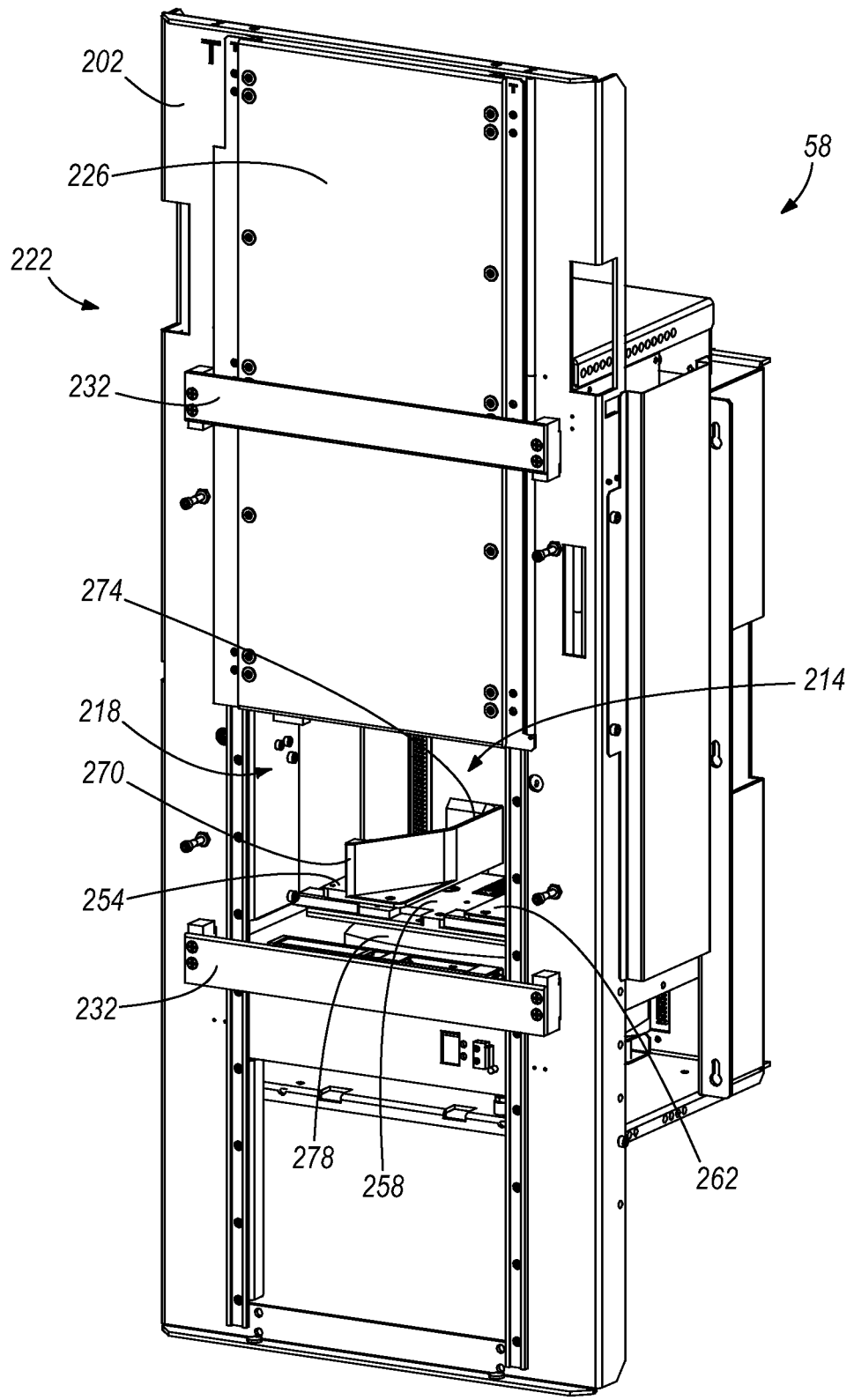
FIG. 22 is a front perspective view of the user access assembly of the pharmaceutical storage and retrieval system illustrated in FIG. 3.

The user access assembly 58, illustrated in FIGS. 17-28 includes a frame 202 supporting a first port 206 having a first opening 210 (See FIG. 19) and a second port 214 having a second opening 218 (See FIG. 22). Additional or fewer ports are also possible in alternative constructions. The user access assembly 58 further includes a door assembly 222 having a front door 226 and a rear door 230.

Figure 17:
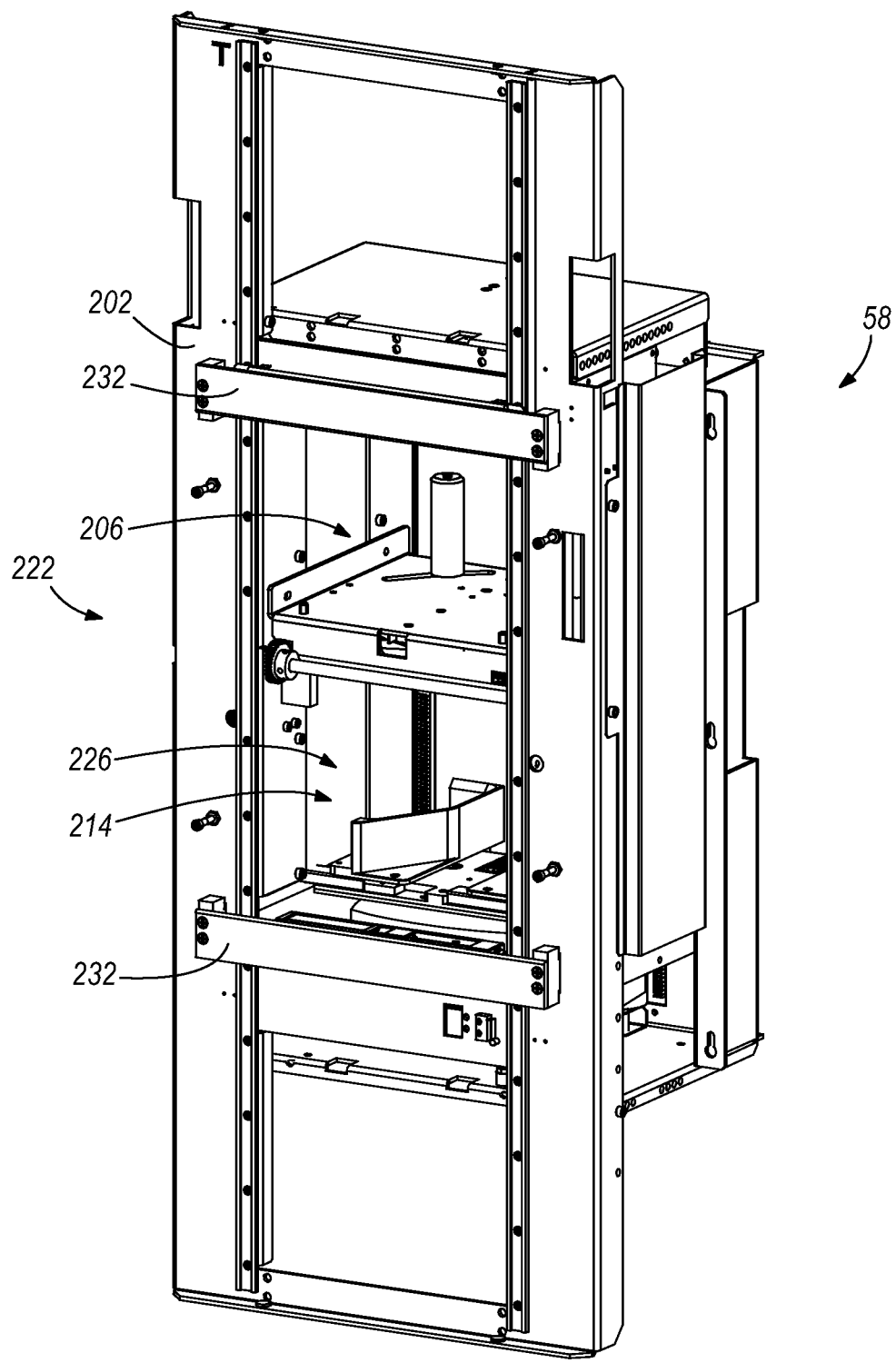
FIG. 17 is a front perspective view of a user access assembly of the pharmaceutical storage and retrieval system illustrated in FIG. 3.
Figure 18:
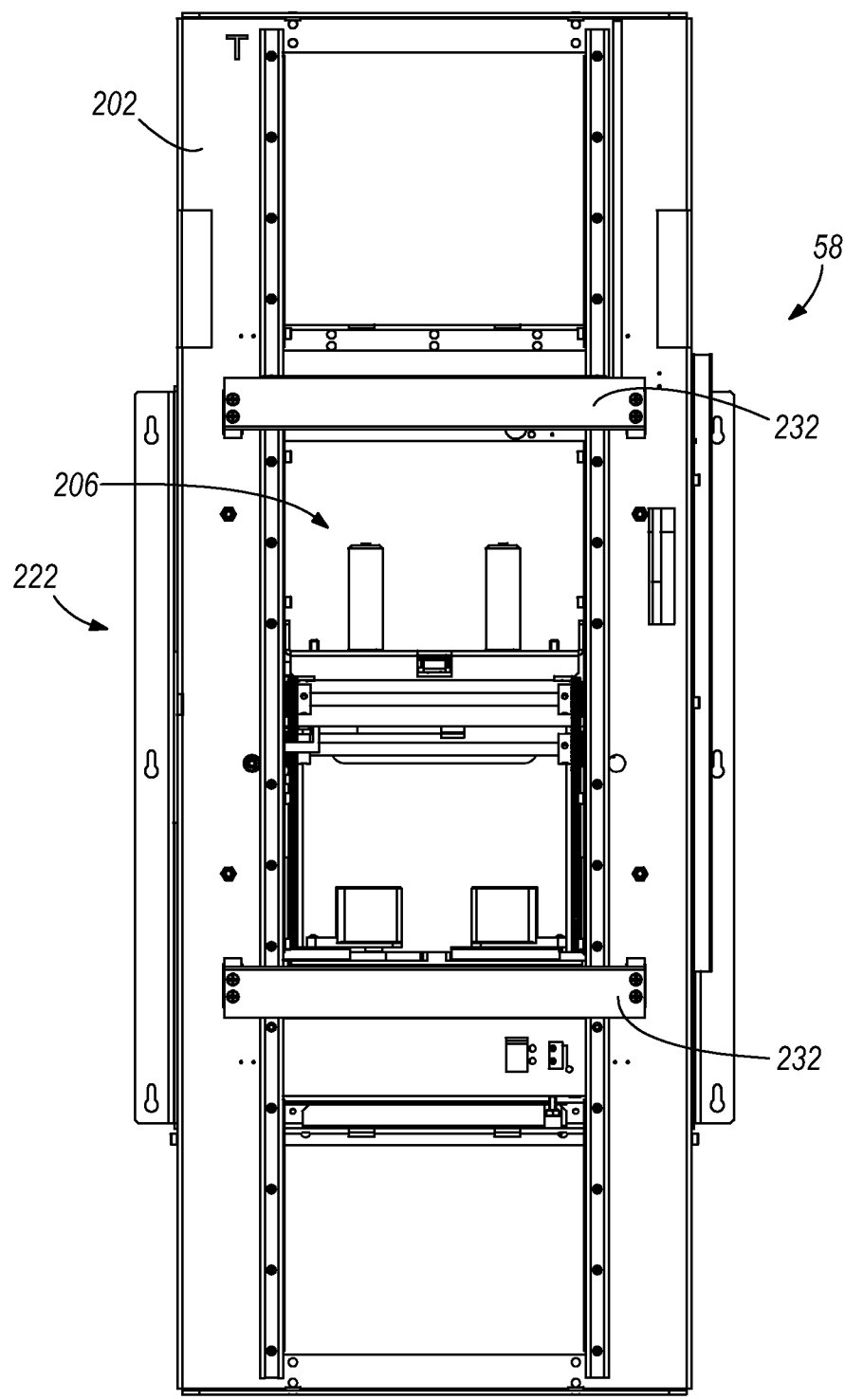
FIG. 18 is a front view of the user access assembly of the pharmaceutical storage and retrieval system illustrated in FIG. 3.
Figure 19:
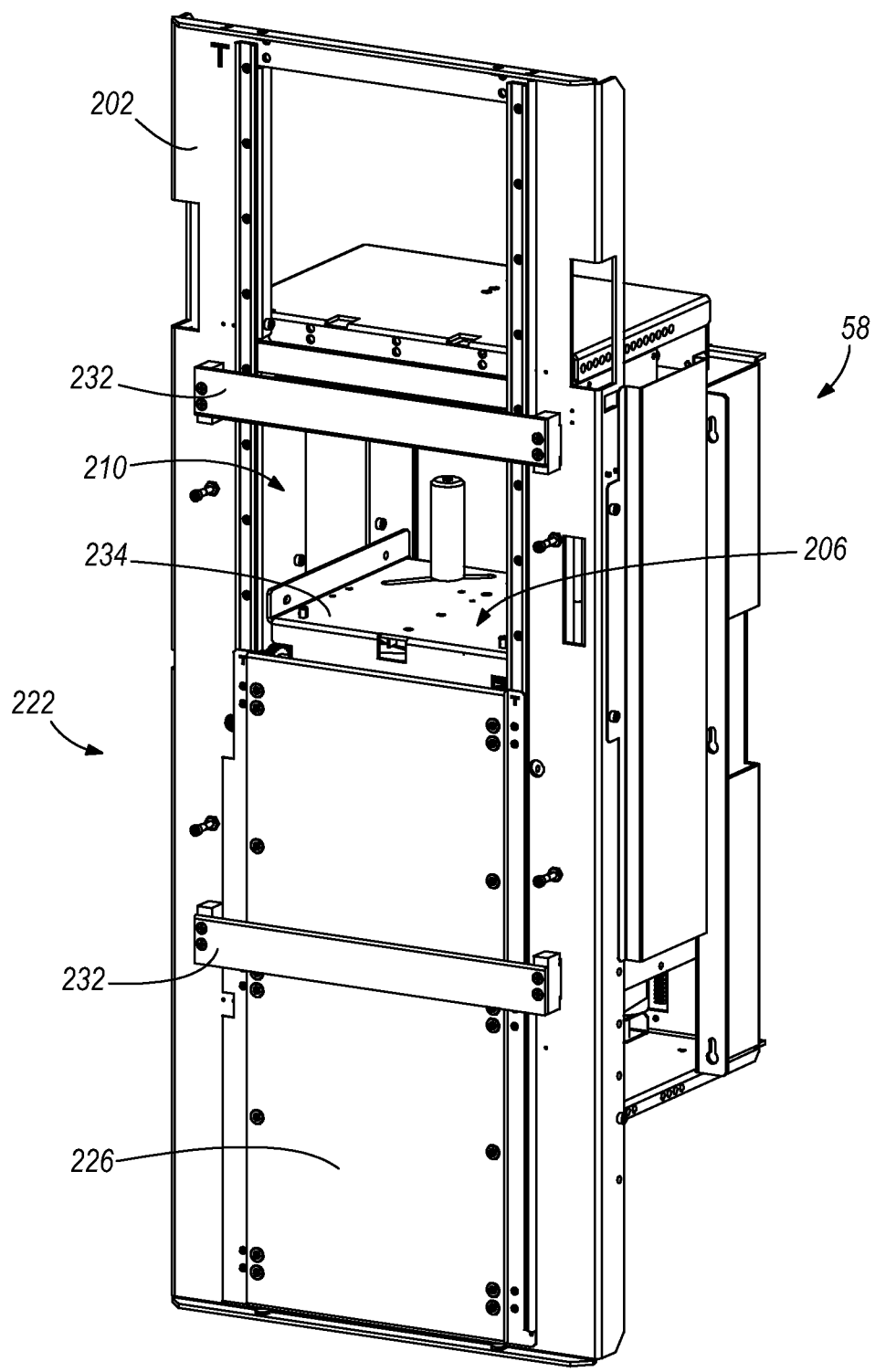
FIG. 19 is a front perspective view of the user access assembly of the pharmaceutical storage and retrieval system illustrated in FIG. 3.
Figure 23:
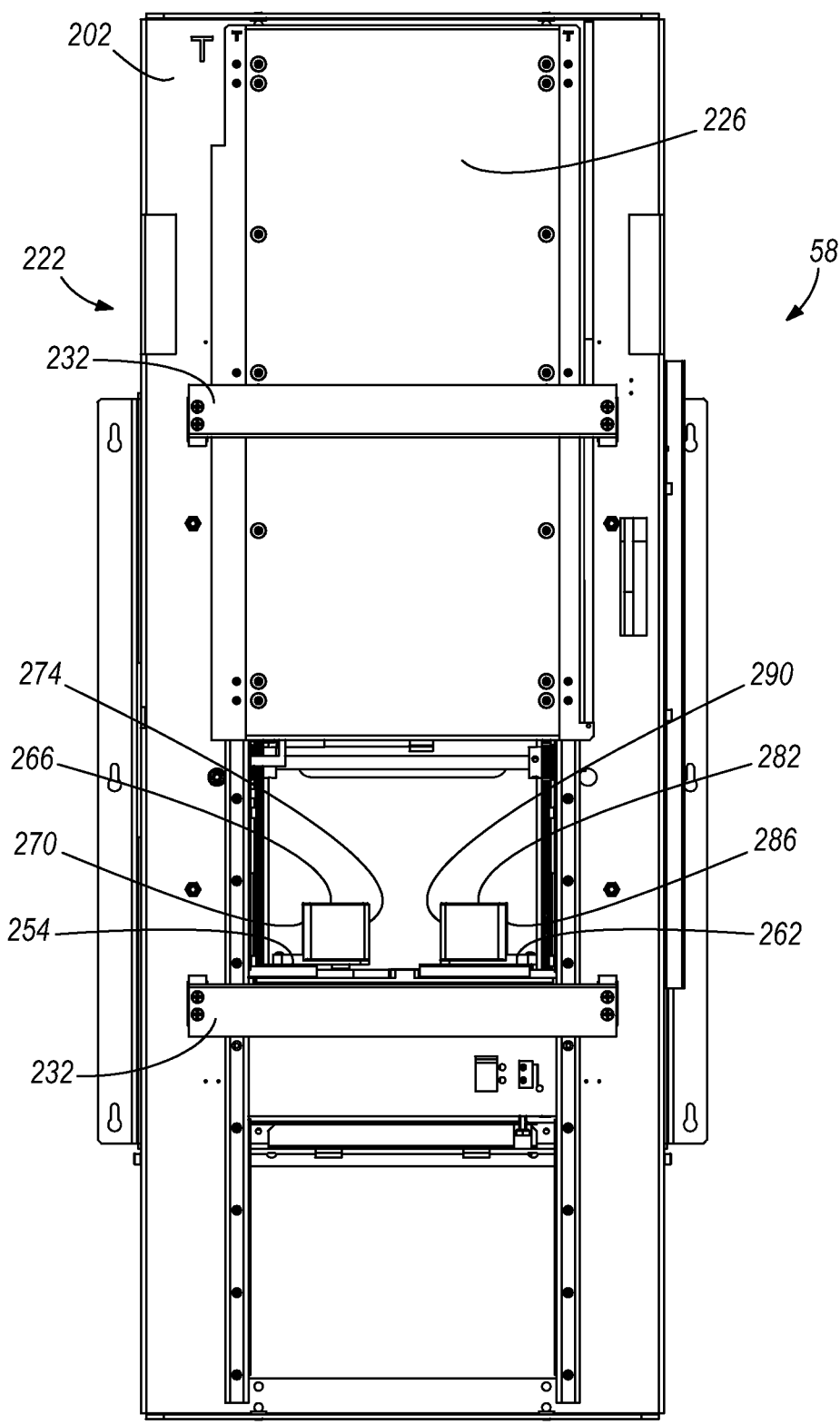
FIG. 23 is a front view of the user access assembly of the pharmaceutical storage and retrieval system illustrated in FIG. 3.

As shown in FIGS. 17-20, 22, and 23, the front door 226 is moveable between a first upper position and a second lower position (and all positions in between) to provide selective access to the first port 206 and the second port 214. The front door 226 moves in a vertical direction (i.e., along the second axis). FIGS. 17-18 illustrate the front door 226 in a home position where the front door 226 covers and prevents user access to the first port 206 and the second port 214. FIGS. 19-20 illustrate the front door 226 in the lower position with a view to the interior of the first port 206 while user access to the second port 214 is closed. FIGS. 22-23 illustrate the front door 226 in the upper position with a view to the interior of the second port 214 while user access to the first port 206 is closed.

Figure 24:
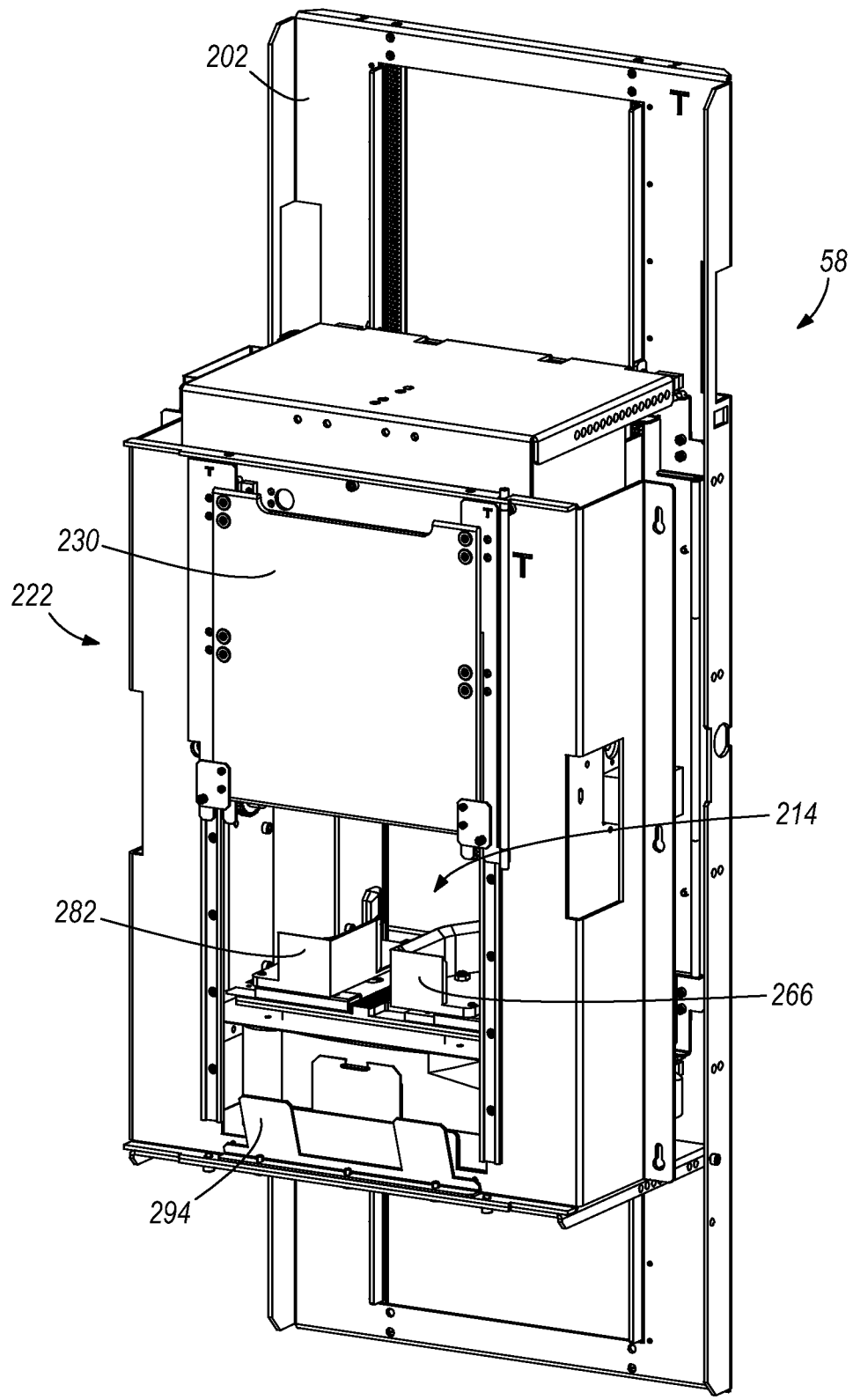
FIG. 24 is a rear perspective view of the user access assembly of the pharmaceutical storage and retrieval system illustrated in FIG. 3.
Figure 25:
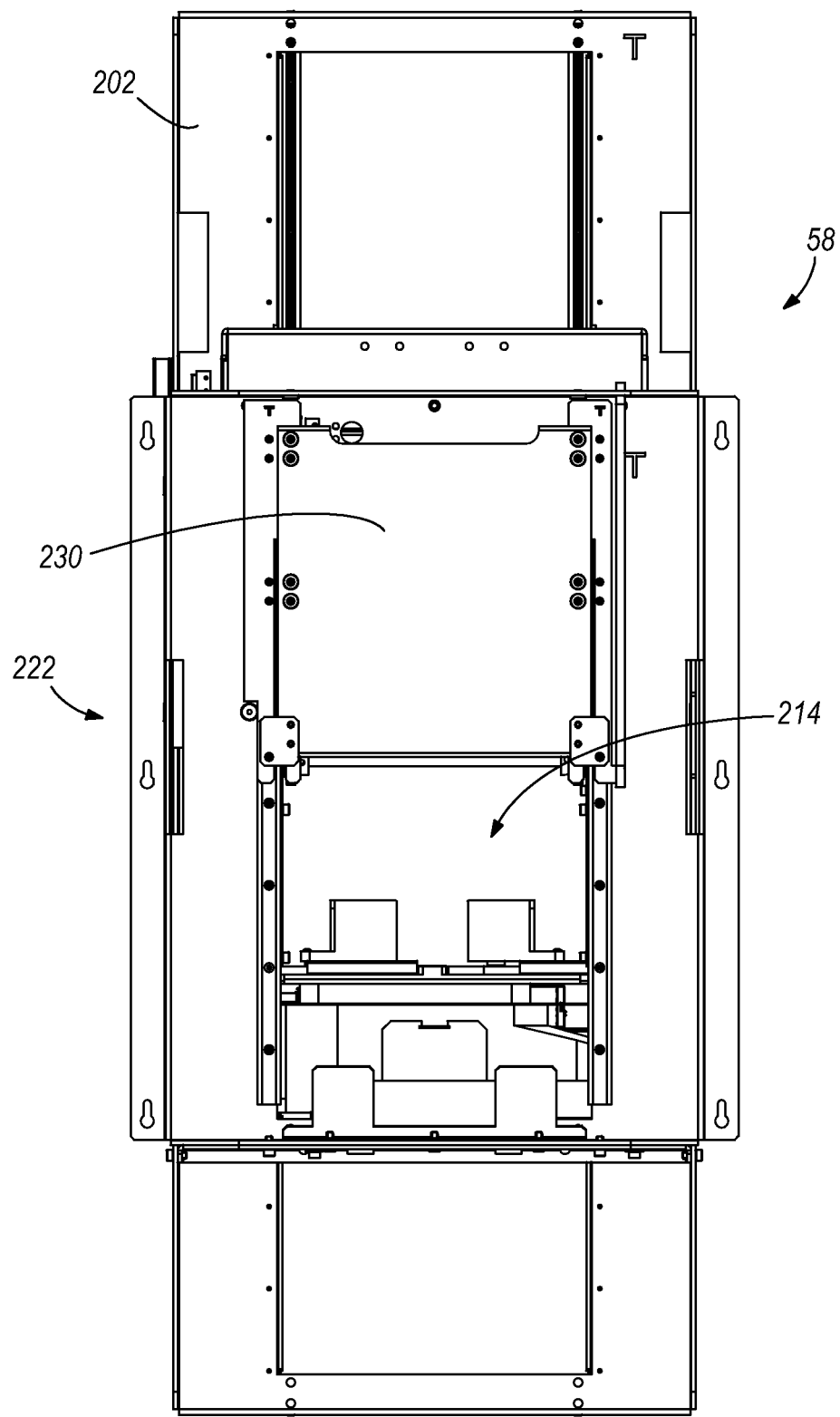
FIG. 25 is a rear view of the user access assembly of the pharmaceutical storage and retrieval system illustrated in FIG. 3.
Figure 26:
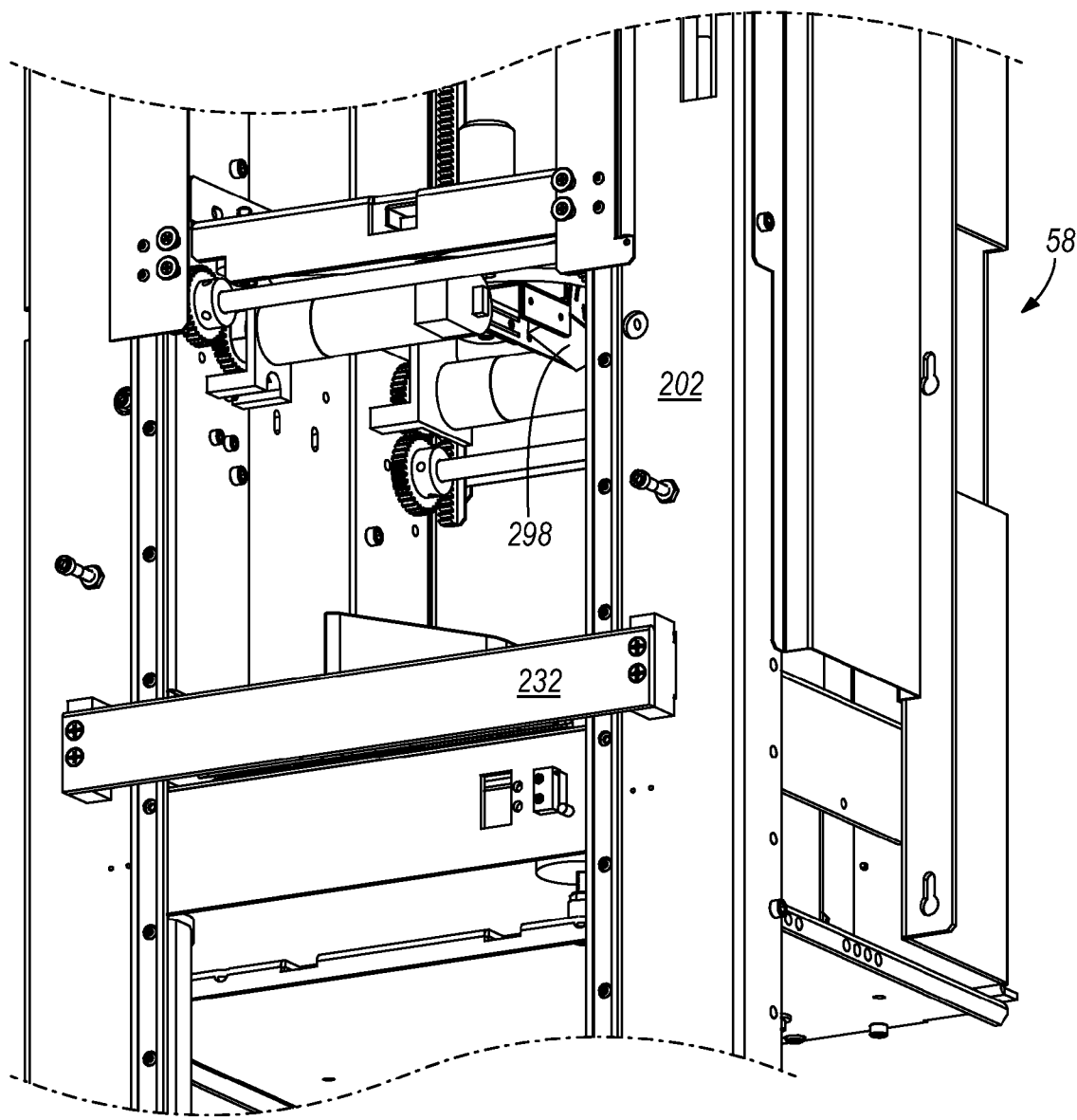
FIG. 26 is an enlarged bottom perspective view of a portion of the user access assembly of the pharmaceutical storage and retrieval system illustrated in FIG. 3.
Figure 27:
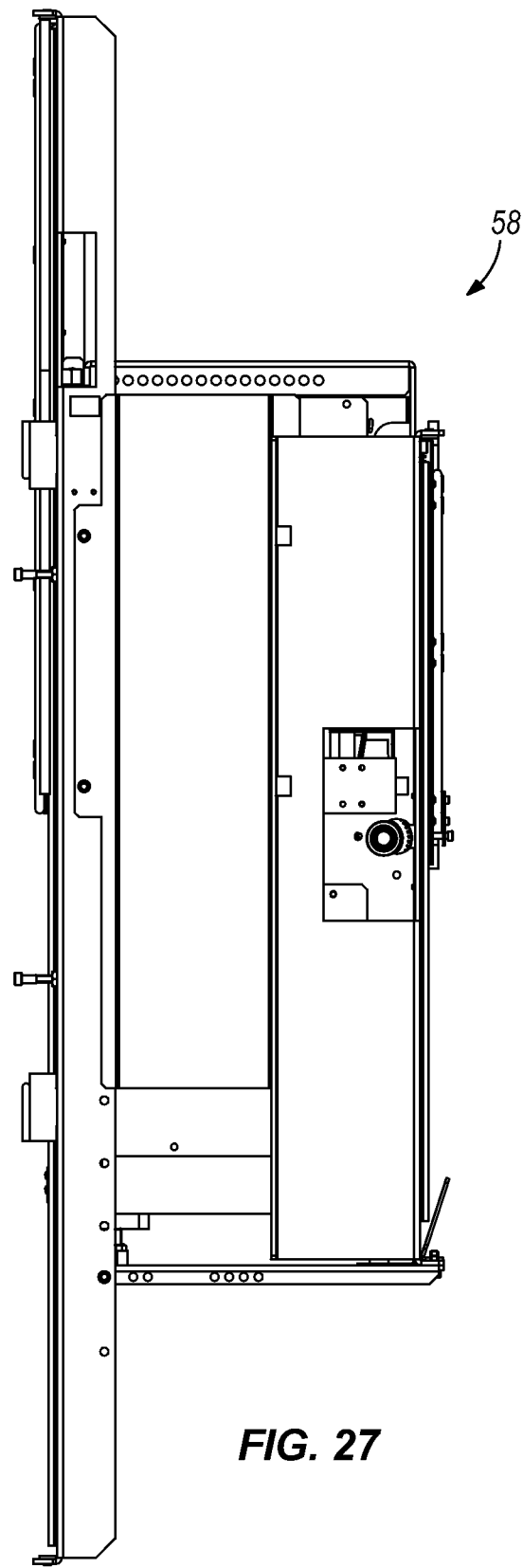
FIG. 27 is a right side view of the user access assembly of the pharmaceutical storage and retrieval system illustrated in FIG. 3.
Figure 28:
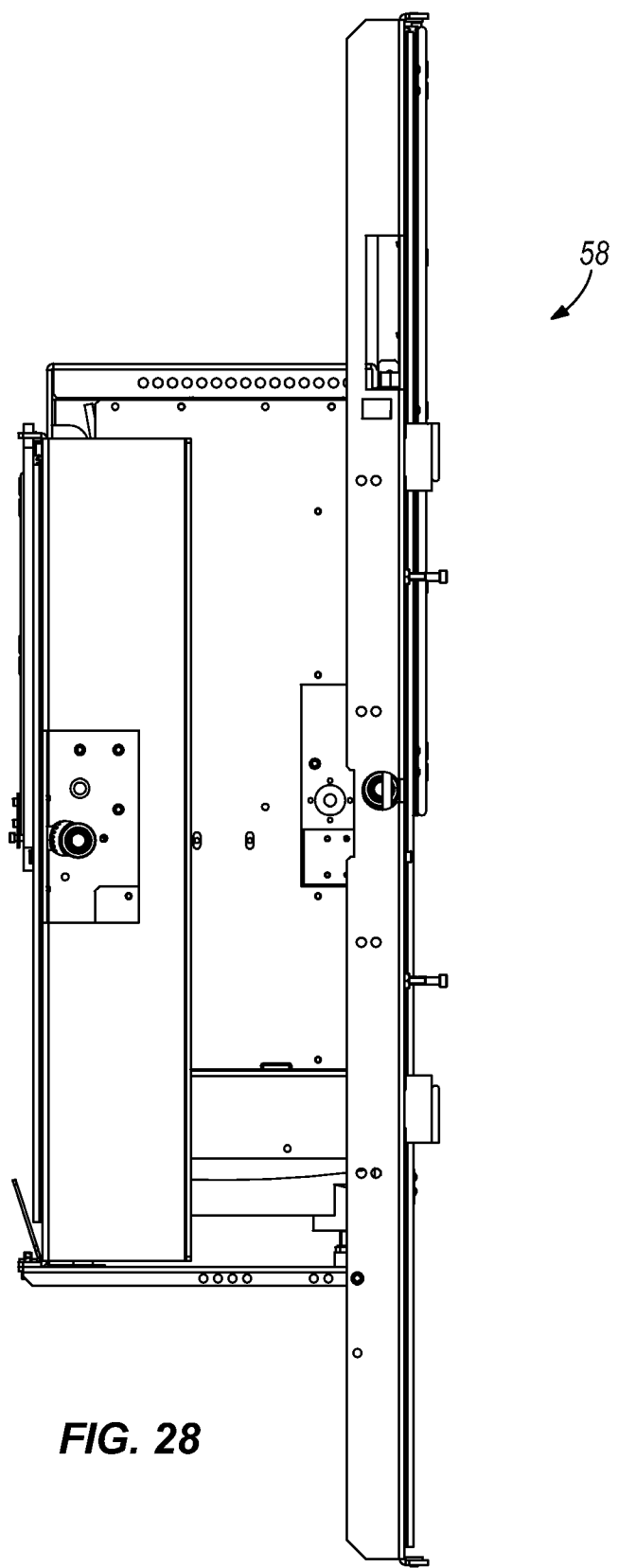
FIG. 28 is a left side view of the user access assembly of the pharmaceutical storage and retrieval system illustrated in FIG. 3.

As shown in FIGS. 21, 24, and 25 the rear door 230 is moveable between a first upper position and a second lower position (and all positions in between) to provide the gripper assembly 166 selective access to the first port 206 and the second port 214. The rear door 230 moves in a vertical direction (i.e., along the second axis), and is smaller than the front door 226 in terms of its height. Generally, the rear door 230 is about half the height of the front door 226. FIG. 21 illustrates the rear door 230 in the lower position with a view to the interior of the first port 206 while gripper assembly 166 access to the second port 214 is closed. FIGS. 24-25 illustrate the rear door 230 in the upper position with a view to the interior of the second port 214 while gripper assembly 166 access to the first port 206 is closed.

The front door 226 and the rear door 230 operate in a coordinated manner. User access to the ports 206, 214 depends on instructions input to the device 14 and whether the gantry assembly 54 is in a retrieval mode or a put-away mode (both modes discussed in more detail below). For example, when a user is granted access to retrieve a container 94 from the first port 206, the front door 226 will move to its lower position to open access to the first port 206 while the rear door 230 remains in its upper position. This configuration prevents a user from reaching inside the device 14 through the first port 206 for a container 94 that is near the doors 226, 230. Further, this configuration prevents user injury by avoiding inadvertent contact between the user and the gantry assembly 54, the gripper assembly 166, and other moving parts within port 206. As another example, when the user is accessing the second port 214 to put-away a container via the second port 214, the front door 226 will move to its upper position to open access to the second port 214 while the rear door 230 moves to its lower position. Again, this configuration prevents a user from reaching inside the device 14 through the second port 214 for a container 94 that is near the doors 226, 230. As noted above, this configuration further prevents user injury by avoiding inadvertent contact between the user and the gantry assembly 54, the gripper assembly 166, and other moving parts within port 214.

The first port 206 and the second port 214 include a detection device, for example, a light beam break sensor, that detects the presence of an object (e.g., a container or a user's hand) in the port and prevents the front door 226 from moving. The first port 206 and the second port 214 also include a safety bar 232. In the event that the front door 226 is moving and the user's hand remains in the port opening, the safety bar 232 moves downward as the door 226 impinges on the hand and stops movement of the door 226.

With reference to FIGS. 19 and 21, the first port 206 is configured to receive a container 94 from the gripper assembly 166 and to allow a user to pick-up the container 94 (as it is likely needed to fill a prescription). The first port 206 includes a base 234 having a first slot 238 and a second slot 242. A first end of the slots 238, 242 is at a predetermined distance from the center line of the base 234. The slots 238, 242 are oriented on a diagonal and extend outward toward the side walls 42, 46 of the device 14 (when viewed from inside the device 14) to a second end of the slots 238, 242.

With reference to FIG. 21, the first slot 238 is configured to receive a pin attached to a first member 246, and the second slot 242 is configured to receive a pin attached to a second member 250. As the pins move in their respective slots 238, 242, the first member 246 and the second member 250 also move in a coordinated manner. At rest (i.e., when the pins are located at their respective first ends), the second member 250 is spaced a predetermined distance from the first member 246 as defined by the location of the pins in their respective slots 238, 242. The pins are biased to a first position (i.e., at their respective first ends of the slots) in their respective slots 238, 242. The pins can slide within their respective slots 238, 242 as pressure is applied to the first member 246 and the second member 250 from the rear side. As the pins slide under the application of pressure (such as when the gripper assembly 166 moves a container 94 into contact from the rear side (i.e., from inside the device 14) with the first member 246 and the second member 250), the predetermined distance between the first member 246 and the second member 250 widens or gets larger. As the gripper assembly 166 continues pushing the container 94 into the first port 206, the container 94 slides between the first member 246 and the second member 250, and the pins follow their respective slots to move the first member 246 and the second member 250 from their initial position to gradually increase the predetermined distance until the container fits between the first member 246 and the second member 250. When the gripper assembly 166 releases its grip on the container 94, the container 94 is held between the first member 246 and the second member 250. Accordingly, in the event that the container 94 is not removed from the first port 206 by an operator, the gantry 54 and the gripper assembly 166 may retrieve the container 94 from the location where the container 94 is held between the first member 246 and the second member 250. The gantry 54 and the gripper assembly 166 may be instructed by the controller 18 to retrieve a container 94 from the first port 206 for a variety of reasons, including, for example, if the operator has not removed the container within a specified time period, or if the operator has requested a different container 94 for retrieval.

With continued reference to FIG. 21, as the container 94 is removed from the first port 206, the pins follow their respective slots 238, 242 to return to their biased first position and to gradually move the first member 246 and the second member 250 to their original position. The height of the first port 206 (which is substantially similar to the height of the second port 214) and the maximum distance between the first member 246 and the second member 250 define the size of a container 94 that can be stored within the device 14. As long as the maximum diameter or width of a container 94 fits between the first member 246 and the second member 250 when the pins are at their respective second ends, then the container 94 can be stored within the device 14. As noted above, containers 94 that do not fit within these parameters can be stored in another safe location in the pharmacy.

In some embodiments, the position of the first member 246 and the second member 250 (or their respective pins) is communicated to the computer 18. The software operating on the computer 18 can perform a mathematical computation to determine the dimension of the container 94 portion that is positioned between the first member 246 and the second member 250. Accordingly, the computer 18 can determine a size of the container 94 based on the location of the pins in their respective slots. The computer 18 may further store the derived measurement in a database.

The first port 206 can include a scanner (or other image or data acquisition device) operatively coupled to the computer 18 and operable to acquire data, including, for example an image of a container 94 positioned on the base 234. The computer 18, by software operating on the computer 18, can use the data to derive measurements of the container 94 and determine one or more dimensions of the container 94. The computer 18 can store the measurement(s) and/or dimensions of the container 94 in a database. The scanner is further operable to read a label, such as a label 114, on the container 94, which allows the computer 18 to verify that the correct container 94 was retrieved by the gantry assembly 54 and inserted into the first port 206. The first port 206 can include a scale (built into or positioned on the base 234) operatively connected to the computer 18 and operable to measure a weight of the container 94 (and its contents) while resting on the base 234. Accordingly, the computer 18 can obtain the weight measurement and alert the user whether the container 94 includes enough of the pharmaceutical to fill the prescription at hand. The computer 18 may further store the weight measurement in a database.

With reference to FIGS. 22-26, the second port 214 is configured to receive a container 94 from the user that is then retrieved by the gantry assembly 54 and the gripper assembly 166 and put away on one of the shelves 66 at an appropriate location determined by the computer 18. With specific reference to FIG. 22, the second port 214 includes a first base 254, a second base 258, and a third base 262.

As shown in FIGS. 22 and 23, the first base 254 is configured to support a first guide member 266 having a first portion 270 (which is angled or oriented on a diagonal with respect to a center line of the port 214 that runs parallel to the x-axis) and a second portion 274 oriented substantially parallel with respect to the center line of the port 214. The first base 254 is configured to move toward and away from the second base 258 in a coordinated motion with the third base 262, such that the first base 254 and third base 262 are synchronized to move toward and away from the second base 258 the same distance.

As shown in FIG. 22, the second base 258 is positioned between the first base 254 and the third base 262. The second base 258 is or includes a built-in scale 278 operatively connected to the computer 18 and operable to measure a weight of a container 94 (and the contents therein) positioned in the second port 214. Software operating on the computer 18 can use the measured weight to verify whether the correct number of pills or amount of pharmaceutical was removed from the container used to fill the particular prescription at hand. This information can be stored in a database.

As shown in FIGS. 22 and 23, the third base 262, positioned opposite the first base 254, is configured to support a second guide member 282 having a first portion 286 (which is angled or oriented on a diagonal with respect to a center line of the port 214 that runs parallel to the x-axis) and a second portion 290 oriented substantially parallel with respect to the center line of the port 214. The third base 262 is configured to move toward and away from the second base 258 in a coordinated motion with the first base 254, such that the first base 254 and third base 262 are synchronized to move toward and away from the second base 258 the same distance.

With reference to FIGS. 22 and 23, the first portions 270, 286 of the guide members 266, 282 are oriented on a diagonal and extend toward the center line (that extends along the x-axis) when viewed from outside the device 14. A first end of the first portions 270, 286 of the guide members 266, 282 is positioned a predetermined distance from the center line. From the first ends of the first portions 270, 286 of the guide members 266, 282, the first portions 270, 286 gradually extend toward the center line until they intersect with the second portions 274, 290 of the guide members 266, 282.

The first guide member 266 and the second guide member 282 move in a coordinated manner. The first and second guide members 266, 282 are biased to a first position such that the second portions 274, 290 are spaced a predetermined distance apart. The guide members 266, 282 can slide open or away from the center line as pressure is applied to the first guide member 266 and the second guide member 282 from the front side of the device 14. As the guide members 266, 282 slide open under the application of pressure (such as when the user inserts a container 94 into the second port 214 from the front side of the device 14), the predetermined distance between the first guide member 266 and the second guide member 282 widens or gets larger. As the user continues pushing the container into the second port 214, the container slides between the first portions 270, 286 of the first guide member 266 and the second guide member 282 until the container fits between the second portions 274, 290 of the first member 266 and the second member 282. When the user releases the container 94, the container 94 remains snug between the first guide member 266 and the second guide member 282. The first member 266 and the second member 282 hold the container 94 in a position within the second port 214 that allows a scanner 298 (discussed below) to obtain data regarding the container 94 so that the controller 18 can identify the container 94. In the event that the container is not properly placed within the second port 214 (e.g., the barcode on the container 94 is not positioned such that it can be read by the scanner 298), the device 14 will alert the operator to reposition the container 94. After the container 94 has been identified the gantry assembly 54, and specifically the gripper assembly 166, removes the container from the second port 214. As the container 94 is removed from the second port, the guide members 266, 282 return to their biased first position.

Similar to the discussion above regarding the first port 206 and the first and second members 248, 250, the height of the second port 214 and the maximum distance between the guide members 266, 282 define the maximum size of a container 94 that can be stored within the device 14. As long as the maximum diameter or a width of a container 94 fits between the first guide member 266 and the second guide member 282 when the guide members 266, 282 are at their widest or greatest opening, then the container 94 can be stored within the device 14. As noted above, containers 94 that do not fit within these parameters can be stored in another safe location in the pharmacy.

When a user inserts a container 94 into the second port 214, the rear door 230 is in its lower or closed position. The rear door 230 limits how far a container may be inserted into the port 214. When the cap 102 on the container 94 makes contact with the rear door 230 and after the operator removes his or her hand, the rear door 230 moves away from the second port 214 by sliding up or following a ramped portion 294 to provide a gap between the cap 102 and the rear door 230. As a result of providing this gap, the rear door 230 does not interfere with any measurements made of the container 94 while the container 94 is in the second port 214, including, for example weight measurements taken of the container 94. While the container 94 rests in the second port 214, the scale 278 can measure the weight of the container 94. As discussed above, the scale 278 may further communicate the measured weight of the container 94 to the computer 18, which may be further stored in a database.

The second port 214 also can include a scanner 298, such as a barcode scanner (or other image or data acquisition device) operatively coupled to the computer 18 and operable to acquire data including, for example the data contained on a label 114 to obtain the NDC to verify the contents of the container 94 being returned to the device 14. The second port 214 may include one or more additional scanners 298 for gathering data, including, for example, laser line scanners, ultrasonic sensors, and whisker or wire scanners. In addition, the second port 214 can include a camera to acquire an image of the container 94 for verification purposes. The computer 18 can store the data from the scanner and the images (if taken) in a database. The software can further associate the data collected from the label 114 with other data collected by the computer 18, including for example the measured weight of the container 94 as returned to the device 14. This information can be further stored in a database.

The user access assembly 58 includes a fan assembly having a replaceable filter element connected to the frame 122. The fan assembly operates to lightly pressurize the device 14 so air blows out of the device 14 when the doors 226, 230 open. The fan assembly also operates to keep dust out of the device 14. Accordingly, the fan assembly helps maintain the cleanliness of the shelves 66, such that the pharmacist and staff do not have to periodically wipe down the shelves, as is normally required by protocol. The fan assembly further operates to maintain the same temperature and humidity levels within the device as exist within the pharmacy.

Figure 29:
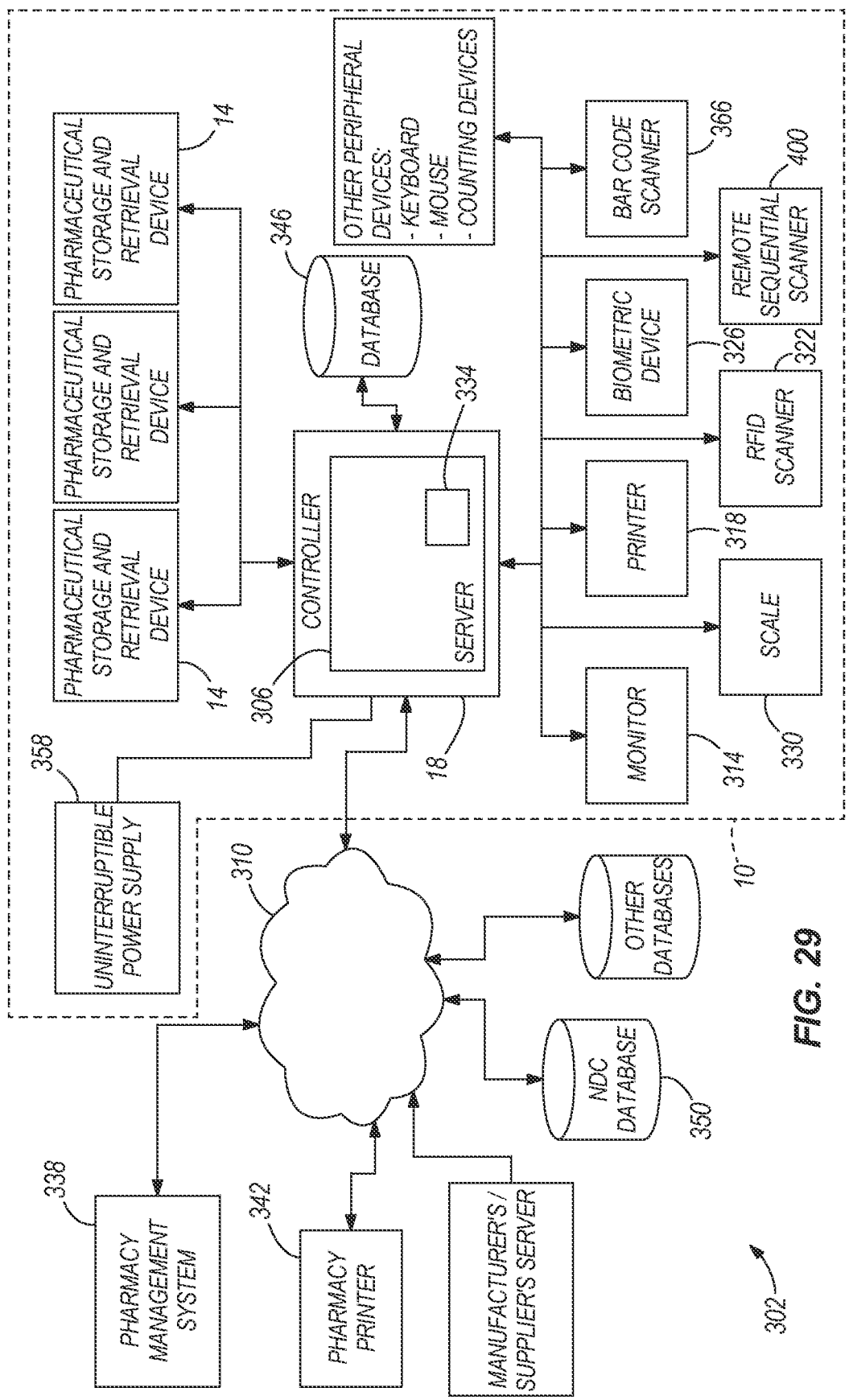
FIG. 29 is a schematic of a pharmacy incorporating the pharmaceutical storage and retrieval system illustrated in FIG. 3.

FIG. 29 schematically illustrates the pharmaceutical storage and retrieval system 10 and its functionality within a pharmacy 302. As noted above, the pharmaceutical storage and retrieval system 10 includes one or more pharmaceutical storage and retrieval devices 14 and a computer or controller 18 configured to control operations and functionality of the pharmaceutical storage and retrieval devices 14. The two-way arrows in FIG. 29 generally represent two-way communication and information transfer between the pharmaceutical storage and retrieval system 10, its subcomponents, including for example, controller 18, and other devices external to the pharmaceutical storage and retrieval system 10. However, for some medical and computerized equipment, only one-way communication and information transfer may be necessary.

As shown in FIG. 29, the controller 18 includes a server 306 in communication with the pharmaceutical storage and retrieval device 14, a network 310, and a plurality of peripherals, such as a monitor 314 (e.g., with touch screen capability), a printer 318, and an RFID scanner 322. In other embodiments, the server 306 can be external to the controller 18. As shown in FIG. 29 other peripherals can include a biometric device 326 and a scale 330 amongst other suitable peripherals. The controller 18 and/or server 306 can further be in communication with any suitable input/output device adapted to be accessed by pharmaceutical personnel, including, for example, a remote sequence scanner 400, a bar code scanner 366, and automated counting devices, such as vibratory and visual counting devices. The controller or computer 18 can include typical hardware such as a processor, I/O interfaces, and storage devices or memory. The controller 18 can also connect to and communicate with input devices such as a keyboard and a mouse.

The server 306 includes an operating system for running or executing various software programs (e.g., instructions stored on a computer readable medium) and/or a communications application. In particular, the server 306 can include a software program 334 (or multiple programs) that communicates with the pharmaceutical storage and retrieval device 14 (and various components of the device 14) and with other devices and/or components via the network 310. Alternatively, software program(s) 334 can also reside on a disc or other programmable device that is capable of being read by the server 306 or computer 18. Furthermore, the server 306 can be networked with other servers 306 and pharmaceutical storage and retrieval systems 10. The other servers 306 may include additional and/or different computer programs and software and are not required to be identical to the server 306, described herein.

The pharmaceutical storage and retrieval system 10 can communicate with a pharmacy management system 338 over the network 310. The pharmacy management system 338 can further communicate with a pharmacy printer 342 over the network 310 as well as with other devices and systems. Alternatively, the pharmacy printer 342 may be directly connected to the pharmacy management system 338. The pharmaceutical storage and retrieval system 10, through for example, the controller 18 and/or server 306, can also communicate via the connection to network 310 with a computer or server operated by the system 10 manufacturer or supplier. Via the connection to the computer or server operated by the system 10 manufacturer or supplier, the system 10 can communicate information regarding operation of the system 10, including, for example, fault codes and error messages, as well as usage and diagnostic data, such as run times, maintenance and service requirements, inventory information, updated pharmaceutical measurement data, etc. The system 10 can also receive operation software from the system 10 manufacturer or supplier via the network 310 connection, including, for example, user interface software, system 10 control software, algorithms, etc. The system 10 can further receive information from the system 10 manufacturer or supplier via the network 310 connection, including for example, updates to database information, such as updates to the National Drug Code database 350 and updates to other databases, including, for example, insurance databases, drug utilization databases, and databases of pharmaceutical container and pill weights. The pharmaceutical storage and retrieval system 10, through for example, the controller 18 and/or server 306, can further communicate with a database(s) 346 and/or other databases such as a National Drug Code database 350, via the connection to network 310. The software program(s) 334 embodying the National Drug Code database 350 can also reside locally on a disc or other programmable device that is capable of being read by the server 306 or computer 18. Such software program(s) 334 embodying the National Drug Code database 350 that reside locally can be regularly updated via the above described connection and communication with the system 10 manufacturer or supplier via the network 310 connection.

The network 310 can be built according to any suitable networking technology or topology or combinations of technologies and topologies and can include multiple sub-networks. Connections between the devices and systems shown in FIG. 29 can be made through local area networks ("LANs"), wide area networks ("WANs"), public switched telephone networks ("PSTNs"), wireless networks, Intranets, the Internet, or any other suitable networks. In a hospital or medical care facility, for example, communication between the devices and systems shown in FIG. 29 can be made through any required communication protocol(s), including, for example, the Health Level Seven ("HL7") protocol or any other version of a required protocol. The HL7 protocol is a standard protocol which specifies the criteria for data exchange (including the required interface implementation) between two computer applications (sender and receiver), such that a universal standard is used by vendors, thereby facilitating the exchange of electronic data in health care environments. The HL7 protocol allows health care institutions to exchange key sets of data from different application systems. Specifically, the HL7 protocol can define the data to be exchanged, the timing of the interchange, and the communication of errors to the application. The formats are generally generic in nature and can be configured to meet the needs of the applications involved.

In the event of power interruption at the pharmacy, the pharmaceutical storage and retrieval system 10 may continue to operate using an uninterruptible power supply ("UPS") 358. Software operating on the controller 18 can determine how many prescriptions can be filled based on the remaining power available from the UPS 358. In particular, while operating under power from the UPS, the operator may access and print a map that identifies the location of each container 94 within a particular device 14. The controller 18 maintains and continually updates the map identifying the location of each container within each device 14, such that the map can be accessed and printed at any time. In the event that there is a complete loss of power to the pharmaceutical storage and retrieval system 10, the pharmaceutical storage and retrieval system 10 includes a manual override function. The manual override function may deactivate a lock 48 to allow access to the housing 22 (see FIGS. 4-6) such that authorized personnel can access the containers 94 within the housing the map to continue filling prescriptions.

User Authorization System

Figure 33:
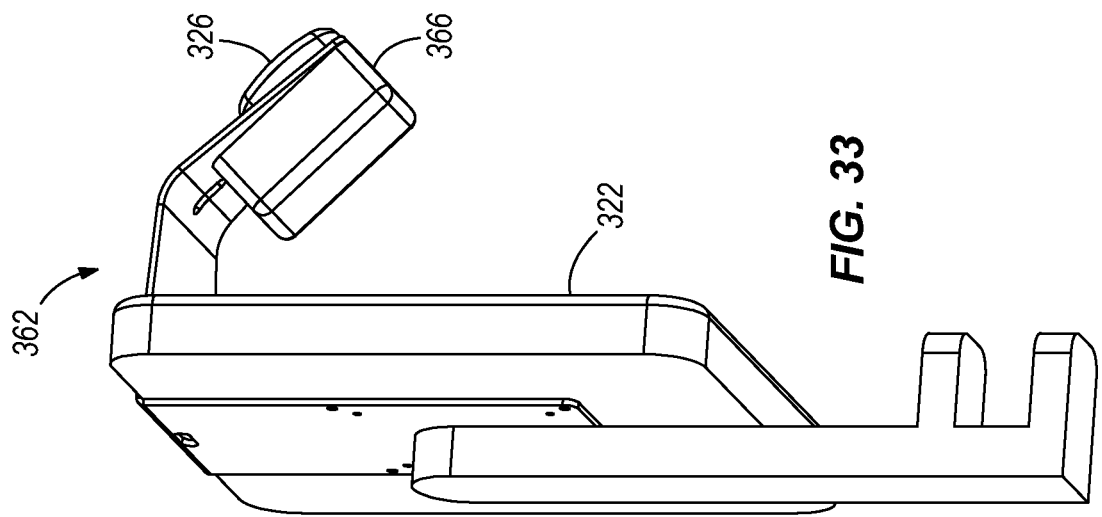
FIG. 33 is a perspective view of a RFID scanner of the pharmaceutical storage and retrieval system illustrated in FIG. 3.
Figure 32:
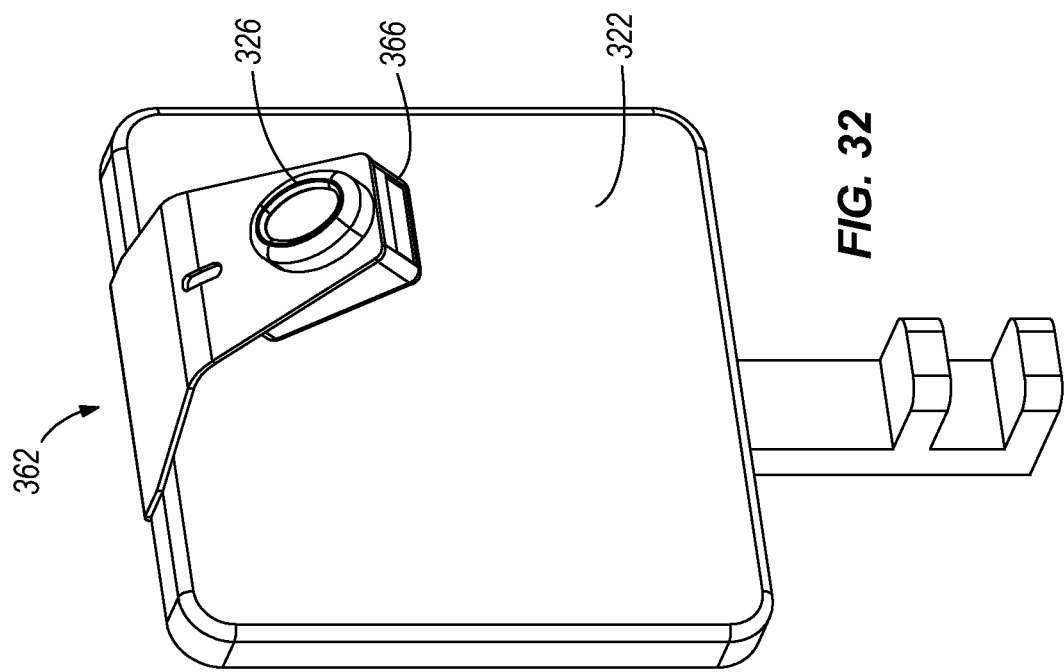
FIG. 32 is a perspective view of a RFID scanner of the pharmaceutical storage and retrieval system illustrated in FIG. 3.

As shown in FIGS. 32 and 33, the pharmaceutical storage and retrieval system 10 also includes a user authorization system 362. As shown in FIGS. 32 and 33, the user authorization system 362 includes an RFID scanner 322, a biometric scanner 326, and a barcode scanner 366. As shown in FIGS. 32 and 33, the RFID scanner 322 is integral with the user authorization system 362. In alternate embodiments, the RFID scanner can be separately located proximate the device 14, including, for example in the first port 206 or the second port 214, or in both ports. The biometric scanner 326 is used to identify an authorized user of the system 10 and can be, for example, a fingerprint scanner, an iris reader, a voice recognition scanner, a facial recognition scanner, or combinations thereof. The barcode scanner 366 can be used in addition to the barcode scanner 298 in the second port 214 to read barcodes such as the NDC on the containers 94 or the labels 114, or other unique identifiers on custom containers.

Each operator of the pharmaceutical storage and retrieval device is assigned a unique RFID credential (and/or other identification). Typically, each operator is assigned his or her unique RFID credential at the start of each shift. The RFID credential is activated and associated with a particular operator after the operator's identity is verified by the controller 18 after reading data obtained by the biometric scanner 322. The RFID credential can be set to expire at a predetermined time, for example, after a set number of hours or at the end of a shift, at which time the credential may be reassigned to a new operator or may be reactivated by the same operator after the operator's identity is re-verified. Accordingly, the RFID credential may be activated and deactivated multiple times and can, for example, be a bracelet that is permanently assigned to an operator. Alternatively, the RFID credential may be temporarily assigned to an operator to be used by another operator at a different time. Still further, the RFID credential can be disposable. While active, the RFID credential is scanned each time an operator interacts with the pharmaceutical storage and retrieval device to retrieve ("check-out") or return ("check-in") a container of medicine. In this manner, the user is associated with the container 94 that is being retrieved from or returned to the device 14. This information is stored in the database for audit and review purposes (e.g., to verify inventory, locate inventory, and investigate possible theft). The RFID credential is also scanned each time the operator interacts with the pharmaceutical storage and retrieval system 10 to access data or to input data into the system. Accordingly, all interaction with the system 10 can be associated with a particular operator, and such interaction can be monitored, tracked, restricted, and audited.

In addition to identifying an operator for the purposes of assigning a unique RFID credential to the operator, the biometric sensing device 326 can be configured to allow access to the system 10 for certain functions, including those functions or interactions permitted with an active RFID credential. In further embodiments, the user authorization system 362 can include other access limiting mechanisms in addition to or in place of the RFID scanner 322, such as, for example, identification card swiping, access code input, or the like. Access to the system 10 and to individual devices 14 can additionally be monitored by a video camera mounted on, within, or separate from the housing 22 of the device 14.

As noted above, the barcode scanner 366 can be used in addition to the barcode scanner 298 in the second port 214 to read barcodes such as the NDC on the containers 94 or the labels 114, or other unique identifiers on custom containers. The barcode scanner 366 can also be used to scan unique barcode labels generated by the system 10 to identify individual containers 94 of particular pharmaceuticals. In such embodiments, the system 10 generates a barcode that is uniquely assigned to each container 94 that is stored in the device 14. As each container 94 is first introduced into the device 14, a label bearing the system 10 generated barcode is affixed to the container 94. Thereafter, each time the container 94 is "checked out" or "checked in" to the system 10, the system 10 cannot only identify the type of medication being "checked out" or "checked in," but can further track the specific container 94. Accordingly, such embodiments of system 10 allow multiple containers 94 of the same pharmaceutical or medication to be "checked out" of the system 10 at the same time. Because the system 10 can identify each specific container 94, the system 10 can associate each container with, for example, a specific operator or a specific prescription order to verify that the order was properly completed. The system 10 generated barcodes can also be scanned by barcode scanners in the first and second ports 206, 214, such as barcode scanner 298.

In still further embodiments, and as discussed further herein, the barcode scanner 366 can be used to read label sheets that are generated by a pharmacy management system 338 following entry of a prescription fill order.

Figure 30:
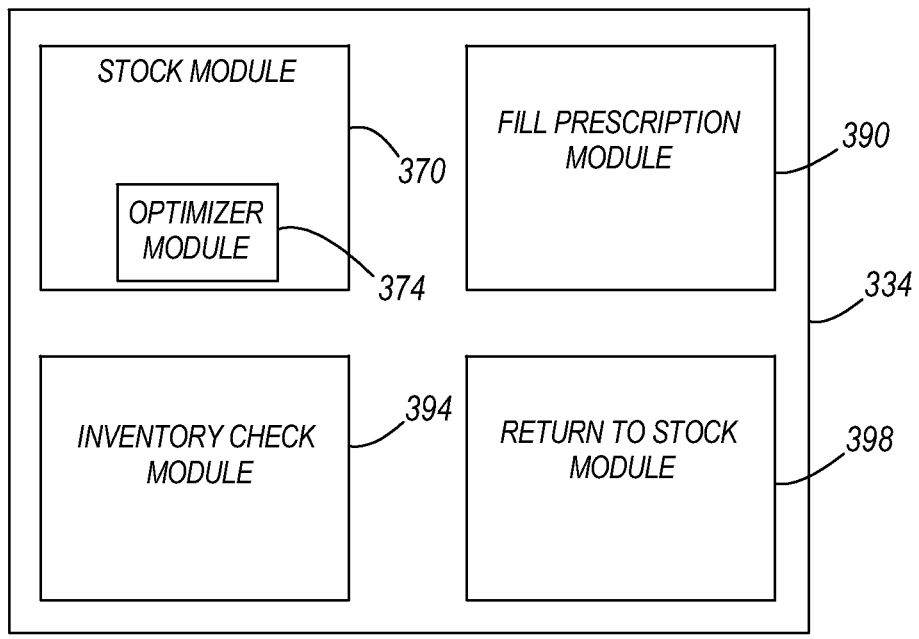
FIG. 30 is a block diagram illustrating a software program for controlling the pharmaceutical storage and retrieval device illustrated in FIG. 3.

As shown in FIG. 30, the software program 334 includes a plurality of modules including a stock module 370, a fill prescription module 390, an inventory check module 394, and a return to stock module 398. The software program 334 and the modules 370, 390, 394, and 398 allow authorized users to interact with the pharmaceutical storage and retrieval device 14, perform prescription filling functions, and conduct other pharmacy business functions related to use of the pharmaceutical storage and retrieval device 14. The software program 334 is accessible by pharmacy personnel via a user interface, including, for example, a user interface displayed on the monitor 314. (See FIG. 29.) The software program 334 can include additional modules, including, for example, a module that facilitates report generation of data collected by the controller 18, including inventory reports, transaction reports, exception reports, etc.

With continued reference to FIG. 30, the stock module 370 is accessible by authorized users to put-away new or existing inventory (i.e., containers) into the pharmaceutical storage and retrieval device 14. In the put-away mode, the user scans the barcode on a container 94 with the barcode scanner 366 at which time the user's RFID credential is also read by the scanner 322. The stock module 370 associates the user with the container 94 and notes that the user put-away the container 94. The stock module 370 is operable to provide instructions to the pharmaceutical storage and retrieval device 14 to retrieve a container 94 resting in the second port 214, grab the container 94, and position the container 94 on a shelf 66 within the device 14. When the controller 18 receives the appropriate signal from the detector in the second port 214 (e.g., a light beam break detector) indicating the absence of a hand in the second port 214, the controller 18 closes the front door 226, opens the rear door 230 and directs the gripper assembly 166 to retrieve the container 94. The stock module 370 also is operable to instruct the scanner 298 to read the barcode on the label 114 of the container 94 while the container 94 is in the second port 214 to verify that the same container 94 that was scanned at scanner 366 is the same container 94 that was actually inserted in the second port 214. If there is a discrepancy, the stock module 370 can alert the user. The stock module 370 also can instruct the scale 278 to obtain a weight measurement of the container 94 that can be stored in the database for future reference (e.g., for inventory and reordering purposes, verification of dispensed amount(s), correction of a miscount, investigation of potential theft, etc.).

Using the weight measurement obtained from the scale 278, the stock module 370 can verify that a new container 94 has an accurate full bottle weight. The stock module 370 verifies the measured weight from scale 278 against a pharmaceutical database containing information for each pharmaceutical that can include, for example, the weight of an unopened container 94 of the pharmaceutical, the weight of the packing material (i.e., the foil, cotton, and preservative) associated with the pharmaceutical, and the individual pharmaceutical pill weight. The pharmaceutical database can include information, for example, provided by pharmaceutical manufacturers, information gathered by the system 10 manufacturer, information gathered by third parties, and information collected and recorded by one or more system(s) 10. The system 10 collects data regarding the full container 94 weight, packing material weight, and the weight of the medication as the system processes containers 94 that are stored therein. Upon initial put-away of a new container 94, the new container 94 is inserted into the second port 214 with its seal intact (i.e., with the foil, cotton, and preservative) to obtain an initial weight measurement, which is stored in the database and used to confirm an accurate full container 94, or bottle weight. During the second put-away, the system 10 is able to determine a more accurate weight measurement of the medication (e.g., the weight of each discrete pill) within the container 94 because the excess packaging material (e.g., the foil, cotton, and preservative have been removed). With each future put-away function and each weight measurement of a particular container 94, the system 10 is further improves the accuracy with which the weight of each pill within a container 94 is determined because the packaging weight remains substantially constant. The weight information can be stored in the database for future use, including, for example, providing a baseline weight measurement of each pill in future shipments of a given medication and to identify possible counterfeit pharmaceuticals.

The stock module 370 is also operable to maintain an inventory list of the containers 94 being input to the device 14. The inventory list can assist pharmacy personnel in reporting discrepancies between orders and what was received. The stock module 370 also can generate inventory and/or restocking requests that the server 306 can transmit to an appropriate system via the network 310. The stock module 370 is further operable to maintain or retrieve information associated with each container 94 of medication, including, for example, the expiration date and lot number of a medication. Based on the information associated with each container 94, the stock module 370 can assist pharmacy personnel by, for example, identifying pharmaceutical inventory near or past its expiration date. The stock module 370 can further assist pharmacy personnel in the efficient use of inventory by selecting medication for dispensing in order of its expiration date, thereby facilitating rotation of pharmaceutical inventory. Further, the stock module 370 can generate a report of all pharmaceutical inventory that is near expiration, enabling pharmacy personnel to select the inventory near expiration for return to the pharmaceutical manufacture or supplier for a refund.

Figure 31:
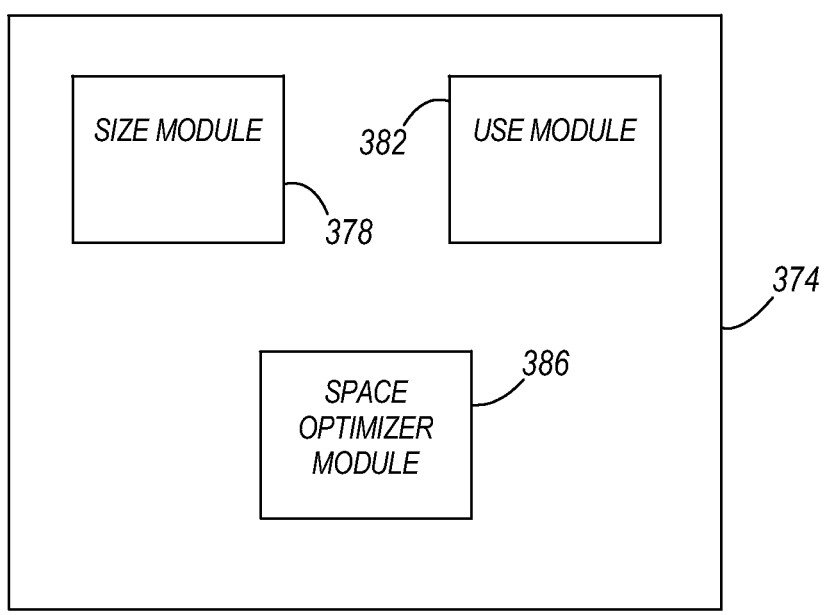
FIG. 31 is a block diagram illustrating a software program for controlling the pharmaceutical storage and retrieval device illustrated in FIG. 3.

As shown in FIG. 30, the stock module 370 further includes an optimizer module 374 operable to determine a location for the container 94 being put-away and stored in the device 14. As shown in FIG. 31, the optimizer module 374 includes a size module 378, a use module 382, and a space optimizer module 386. The size module 378 is operable to instruct a scanner 298 within the second port 214 to obtain data regarding a container 94 therein, including an image of the container 94. The size module 378 is further operable to determine information regarding a container 94, including, for example, a cap 102 diameter, a container 94 shape, and a container 94 size (e.g., height and width) based on the acquired data or image. The size module 378 can also access a database for the size information of the container 94. The use module 382 is operable to determine how frequently the pharmacy utilizes a particular pharmaceutical. The use module 382 can store and access the database 346 for data on how frequently a particular pharmaceutical is utilized. The space optimizer module 386 is operable to receive data from the size module 378 and the use module 382. Using data collected by the system 10, including the data received by the space optimizer module 386 from the size module 378 and the use module 382, the space optimizer module 386 determines a location within the device 14 to store a container 94. The space optimizer module 386 can determine the optimal location within the device 14 to store the container 94 based on frequency of use and/or size of the container 94. Accordingly, the space optimizer module 386 selects a particular location within the devices 14 to allow for efficient storage and retrieval of a particular container 94 when needed. The space optimizer module 386 can determine the location for storing a container 94, each time the container is "put-away" or "checked-in" to the system 10. In such instances, the container 94 may be returned to the location from which it was retrieved, or it may be stored in a new location, including within a different device 14 from which the container was retrieved. The space optimizer module 386 can also randomly determine the location for storing the container 94 within the devices 14, based on available locations. The particular location for each container 94 is stored in the database 346. In further embodiments, the optimizer module 374 may include fewer or more modules for conducting tasks related to the operation of the stock module 370.

As shown in FIG. 30, the software program 334 also includes a fill prescription module 390. The fill prescription module 390 is operable to retrieve a specific container 94 to fill a customer's prescription. When the pharmacy receives a prescription to fill, pharmacy personnel enters the information into the pharmacy management system 338, where the pharmacy printer 342 generates a label sheet that includes the labels for the customer vials, customer information, and a barcode. The label sheet is taken to the scanner 366 where the barcode is read. At the same time, the user's RFID credential can be read to confirm authorization to the system 10 and the pharmaceuticals stored within. Based on the barcode, the fill prescription module 390 instructs the gantry assembly 54 to retrieve the container 94 needed to fill the customer's prescription and identified on the label sheet. More specifically, the fill prescription module 390 communicates with the stock module 370 and/or the database 346 to obtain the particular location where the needed container of medication is stored within the device 14. The fill prescription module 390 further communicates the particular location of the container 94 to the gantry assembly 54 so the carriage assembly 158 knows where to go to retrieve the appropriate container 94. In the instance where a particular container 94 is stored outside the device 14, the external storage location associated with the desired container 94 can be communicated to the operator.

After identifying the particular location of the needed container 94, the gantry assembly 54 retrieves the container 94 and inserts it into the first port 206 and closes the rear door 203. After the user's RFID credentials are verified, the front door 226 opens to allow the user to remove the container 94 from the first port 206. In some constructions, the fill prescription module 390 can instruct the scanner 298 to first read the label 114 on the container 94. The fill prescription module 390 can compare the read data from the label 114 with the required prescription identified on the label sheet. If there is a match, the device 14 activates the front door 226 to open so the user can retrieve the container 94 and count the appropriate number of pills to fill the prescription. If there is no match, the fill prescription module 390 can instruct the device 14 to return the container 94 to its shelf location.

While waiting for the user to remove the container 94, the gantry 54 can be in the process of retrieving another container 94 for the same or a different customer based on the read barcode of a new label sheet. Generally, the gantry assembly 54 retrieves containers 94 in the order in which the label sheets are read at the scanner 366 thereby generating a queue. The queue can be modified by accessing the fill prescription module 390 to adjust the order of the queue. For example, if a customer is waiting to pick-up a prescription, the label sheet for this customer's prescription can be scanned and moved to the top of the queue to be filled immediately. Further, the fill prescription module 390 also is operable to review the data in the queue to group various prescription entries together to prevent the customer from having to make several trips to the pharmacy. The queue can also be modified using the remote sequence scanner 400. Using the remote sequence scanner 400, a user can take multiple label sheets and prioritize the order of prescriptions to be filled by scanning the label sheets in the order the user wishes to fill the prescriptions. The scanned sequence of orders is communicated to the controller 18, which can direct the device 14 to begin retrieving and staging containers 94 needed for the scanned orders. The user can also access the queue using the remote sequence scanner 400 to edit the queue, including, for example, to delete orders, to enter new orders, or to reprioritize the queue.

The pharmacy management system 338 can also communicate the order information directly to the controller 18 of system 10, which can direct the device 14 to begin retrieving and staging containers 94 needed for the entered orders. Similar to the process described above, the user can take a label sheet generated by the pharmacy printer 342 to the scanner 366 where the label sheet barcode and the user's RFID are read. If the system 10 recognizes a valid RFID credential and a barcode on the presented label sheet associated with a staged order, the first port(s) 206 containing the pharmaceutical(s) need to fill the order are opened. Accordingly, the system 10 can be configured to retrieve, but not allow access to the needed pharmaceuticals before the label sheet and RFID are scanned.

If the pharmacy utilizes more than one pharmaceutical storage and retrieval device 14, the containers 94 can be staged amongst the devices 14 based on the order in which the label sheets are read. While one device 14 is waiting for the user to remove a container 94, the other devices 14 can retrieve containers 94, thereby eliminating the time pharmacy personnel has to wait for a given device 14 and its associated gantry assembly 54 to retrieve a container 94. Generally, the gantry assemblies 54 of the devices 14 retrieve the containers according to the order in which customer orders are communicated to the system 10, including, reading label sheets at the scanner 366 to generate a queue, directly communicating orders to the system 10 as they are entered in the pharmacy management system 338, and establishing a queue by scanning label sheets with the remote sequential scanner 400. However, as discussed above, the queue can be modified by accessing the fill prescription module 390 at the controller 18, or through by the remote sequence scanner 400.

Upon completion of the filling process, the container 94 can be immediately returned to the device 14 or the container 94 can remain with the user until the user has time to put-away the container 94. To return a container 94 to the device 14, the user presents his or her RFID credential to the scanner 322, so that the user's access to the system 10 may be verified and the user may be associated with the "put-away" or "check-in" of the container. If the container 94 being returned includes a system 10 generated barcode, the user scans the system 10 generated bar code using scanner 366 allowing the system to identify the specific container that is being returned. The user then positions the container 94 in the second port 214, at which time the system 10 verifies information about the container 94, including, for example, the NDC and the container weight. The system 10 can then "put-away" or "check-in" the container 94. If the container 94 is not returned to the device 14 and another user needs the same container 94 to fill a prescription, the new user can use the container 94, but when the container 94 is put-away by one of the users, the user's RFID credential read at the time of put-away will be associated with the original retrieval of the container 94 and filling of the prescriptions that needed that container 94 until the put-away process is completed as described above.

With continued reference to FIG. 30, the software program 334 includes an inventory check module 394. The inventory check module 394 is operable to maintain a current list of pharmaceuticals within the device 14. The inventory check module 394 also is operable to communicate with the database 346 to request inventory information stored therein. The inventory check module 394, when instructed, can provide a list of all pharmaceuticals within the device 14 and transmit the data to the printer 318 for a readable printout. The pharmacist can use the list to verify what is currently in the device 14. The list is accurate because pharmacy personnel expect the container 94 to be the same when it comes out of the device and when it goes into the device 14; and the device 14 maintains a record of all prescriptions filled and thus, the remaining number of pills remaining in each container 94. The inventory check module 394 also allows the pharmacist to remove each container 94 to check contents and return it to the device 14. Upon return to the device 14, the device 14 verifies the count within the container 94 before storing the container 94.

With further reference to FIG. 30, the software program 334 includes a return to stock module 398. The return to stock module 398 is operable to transmit instructions to the device 14 to accept a customer vial of medication, which was not picked up from the pharmacy. The return to stock module 398 is operable to generate a label for a custom container selected to hold the customer vial(s) as described above. The return to stock module 398 can communicate with the fill prescription module 390 to determine what pharmaceutical is in the vial in order to generate the label. Accordingly, the label generated by the stock module 398 associates the vial and the pharmaceutical contained therein with the custom container. The return to stock module 398 also can communicate with the optimizer module 374 to determine an appropriate location within the device for the custom container and the stock module 370 to instruct the gantry assembly 54 to put-away the custom container. In certain instances, the customer vial can be of a size and construction such that a custom container is not required to hold the vial. In such instances, the customer vial can be handled by the system 10 as if it were a standard container 94.

FIG. 1 illustrates a process of filling a prescription according to conventional dispensing methods. Once a customer drops off a prescription at the pharmacy, a printer generates a label sheet. The printing process repeats for another prescription for another customer regardless of whether the prescription has been filled. The pharmacist or other personnel may attempt to sort the printed label sheets according to pick-up times. However, printed label sheets are generally very difficult to sort, particularly if there are a large number of them. The pharmacist or other personnel takes one of the label sheets and fills the prescription noted thereon. There is no particular fill-order other than the order the label sheets are stacked and no beneficial way to prioritize fill-orders in the event of a rush on the pharmacy during peak times.

With embodiments of the present invention, a user can take a label sheet from the stack, scan the label sheet (and RFID credential), and the gantry assembly 54 will retrieve the needed container 94 according to the label sheet. The user can then fill the prescription, put-away the container 94 and move on to fill the next prescription on the next label sheet.

In the event of a rush on the pharmacy, a user can take multiple label sheets from the stack, scan the label sheets (and RFID credential), and the gantry assemblies 54 of multiple devices 14 can retrieve the needed containers according to the label sheets such that the containers 94 are ready for user retrieval. The user can then quickly fill several prescriptions without waiting for the device to retrieve a container 94. Alternatively, during peak periods, multiple users can take the label sheets, scan the label sheets (and their RFID credential), obtain the container 94 from the first port 206, and return to their station to fill the prescription noted on the label sheet. If a customer's prescription needs to be filled immediately, one of the users can scan that customer's label sheet (and RFID credential), access the queue, and move the label sheet to the top of the queue. The gantry assembly 54 will then retrieve the container 94 for that customer for the user.

Further embodiments of the pharmaceutical storage and retrieval system 10 include a remote sequence scanner 400. Using the remote sequence scanner 400, a user can take multiple label sheets and prioritize the order of prescriptions to be filled by scanning the label sheets in the order the user wishes to fill the prescriptions. The scanned sequence of orders is communicated to the controller 18, which can direct the device 14 to begin retrieving and staging containers 94 needed for the scanned orders. The retrieved containers 94 can be delivered to the first port 206 of each device 14. The front door 226 of each port 206, however, remains closed until the proper label sheet and RFID credential are scanned. If a label sheet is scanned at the device 14 that is not one of the label sheets scanned by the remote sequence scanner 400 or is out of order from the sequence scanned by the remote sequence scanner 400 the device 14 will return the staged container 94, if necessary, and retrieve the container 94 needed to fill the requested order.

In further embodiments, orders entered into the pharmacy management system 338 are directly routed to the system 10. In such embodiments, the pharmacy management system 338 does not print a label sheet. Instead, the user selects the entered order from a queue displayed by the controller 18 on the monitor 314. When an order is selected, the device 14 can retrieve the needed pharmaceuticals and provide them to the user. The system 10 can include a printer that prints a label sheet when the order is selected, or when the needed pharmaceuticals are available to the user from a device 14. The system 10 can also include multiple printers (e.g., a printer associated with each device 14 of the system) located proximate to the first port 206 of each device 14.

In yet further embodiments, as orders are entered, the pharmacy management system 338 will route the order information to the system 10 and direct a printer, such as the pharmacy printer 342, to print an order information sheet that does not include labels for the customer vials. In such embodiments, the user can scan the order information sheet (and RFID credential), and the gantry assembly 54 will retrieve the needed container 94 according to the order information sheet. The system 10 can include a printer that prints the customer vial labels when the needed pharmaceuticals are available to the user from a device 14. The system 10 can also include multiple printers (e.g., a printer associated with each device 14 of the system) located proximate to the first port 206 of each device 14. Further, the system 10 or the pharmacy management system 338 can require that the user scan the order sheet and the retrieved pharmaceutical before a printer will print the customer vial labels.

Further embodiments of the pharmaceutical storage and retrieval system 10 allow for inventory management and monitoring across multiple retail outlets, allowing, for example, a chain of affiliated pharmacies to monitor and manage pharmaceutical inventory for each retail location from a central location or by a central ordering authority. In still further embodiments, system 10 allows for the automated ordering of new stock to replenish depleted pharmaceutical inventory. Further embodiments of system 10 may communicate with a central inventory tracking authority, or with other systems 10, to allow for the transfer of pharmaceutical inventory between retail locations before new inventory is ordered. In still further embodiments, system 10 may be configured for use in non-retail pharmacies, including, for example, in hospitals, in research facilities, in central fulfillment facilities, and in mail order fulfillment facilities.

Further embodiments of the pharmaceutical storage and retrieval system 10 allow for different user access rights, including, for example, different levels of access to different classes of medication, or different levels of access to functional aspects of the system 10. Further embodiments of the system 10 may communicate with a central authority or directly with law enforcement departments in the event that unauthorized or improper access to the system 10 is detected. Such unauthorized or improper access may include, for example, unauthorized physical access to a pharmaceutical storage and retrieval device 14, unauthorized electronic access to a controller 18. The system 10 may also communicate with a central authority or directly with law enforcement departments in the event that the system 10 detects apparent theft based on detected discrepancies in the dispensing of a medication (e.g., the system 10 detects a difference between the prescribed quantity and the amount actually removed from a container 94) or an unusual pattern of medication dispensing.

The embodiments described above and illustrated in the figures are presented by way of example only and are not intended as a limitation upon the concepts and principles of the present invention. Various features and advantages of the invention are set forth in the following claims.

What is claimed is:

1. A pharmaceutical storage and retrieval system comprising:
    a housing including
        a gantry assembly,
        a user access assembly, and
        a user authorization system; and
    a controller operatively connected to the gantry assembly, the user access assembly, and the user authorization system, the controller including a computer having a computer readable medium configured to store instructions that when executed cause the controller to,
        read a user credential via the user authorization system,
        read a unique identifier on a prescription order to determine a container needed to fill a prescription on the prescription order,
        associate the user credential with the unique identifier, and
        transmit an instruction to the gantry assembly to retrieve the container and position the container in the user access assembly;
    wherein the user access assembly comprises a first port and a second port, and wherein the first port receives the container from the gantry assembly; and
    wherein the first port includes a base having a first slot and a second slot, a first member configured to follow the first slot and a second member configured to follow the second slot, and wherein the first member and the second member are biased to a first position, and wherein the gantry assembly applies force to the first member and the second member to move the first member and the second member away from their respective first positions to insert the container into the first port.

2. The system of claim 1 wherein the user credential is a RFID tag.

3. The system of claim 1 wherein the user access assembly comprises a door assembly having a front door moveable between an upper position and a lower position and a rear door moveable between an upper position and a lower position.

4. The system of claim 3 wherein the rear door is in the upper position when the front door moves to the lower position to provide access to the first port.

5. The system of claim 4 wherein the front door moves to the lower position after the user authorization system has read a user credential and the computer associates the user credential with the container in the first port.

6. The system of claim 4 wherein the housing further includes a shelving assembly, and wherein when the rear door is in the upper position, the shelving assembly cannot be accessed via the first port.

7. The system of claim 1 wherein the first member and the second member are configured to adjust to retain pressure on the container and to maintain the container in a predetermined position in the first port.

8. The system of claim 7 wherein when the container is in the predetermined position in the first port, the gantry assembly is configured to retract the container from the first port.

9. A pharmaceutical storage and retrieval system comprising:
    a housing including
        a gantry assembly, and
        a user access assembly, and
    a controller operatively connected to the gantry assembly and the user access assembly, the controller including a computer having a computer readable medium configured to store instructions that when executed cause the controller to,
        read a unique identifier on a prescription order to determine a container needed to fill a prescription on the prescription order, and transmit an instruction to the gantry assembly to retrieve the container and position the container in the user access assembly;

wherein the user access assembly comprises a first port and a second port, and wherein the first port receives the container from the gantry assembly; and wherein the first port includes a base having a first slot and a second slot, a first member configured to follow the first slot and a second member configured to follow the second slot, and wherein the first member and the second member are biased to a first position, and wherein the gantry assembly applies force to the first member and the second member to move the first member and the second member away from their respective first positions to insert the container into the first port.

10. The system of claim 9 wherein the user access assembly comprises a door assembly having a front door moveable between an upper position and a lower position and a rear door moveable between an upper position and a lower position.

11. The system of claim 10 wherein the rear door is in the upper position when the front door moves to the lower position to provide access to the first port.

12. The system of claim 11 wherein the housing further includes a shelving assembly, and wherein when the rear door is in the upper position, the shelving assembly cannot be accessed via the first port.

13. The system of claim 9 wherein the first member and the second member are configured to adjust to retain pressure on the container and to maintain the container in a predetermined position in the first port.

14. The system of claim 13 wherein when the container is in the predetermined position in the first port, the gantry assembly is configured to retract the container from the first port.

* * * * *